(12) United States Patent
Sterimbaum et al.

(10) Patent No.: US 8,227,477 B2
(45) Date of Patent: Jul. 24, 2012

(54) NILOTINIB HCL CRYSTALLINE FORMS

(76) Inventors: Greta Sterimbaum, Rishon-Lezion (IL); Sigalit Levi, Modi'in (IL); Adi Yeori, Tel Aviv (IL); Tamas Koltai, Natanya (IL); Valerie Niddam-Hildesheim, Kadima (IL); Maytal Piran, Rishon Lezion (IL); Shay Asis, Rishon Lezion (IL); Hagit Eisen-Nevo, Shoam (IL); David Malcolm Crowe, Crowthorne (GB)

( * ) Notice: Subject to any disclaimer, the term of this patent is extended or adjusted under 35 U.S.C. 154(b) by 293 days.

(21) Appl. No.: 12/612,943

(22) Filed: Nov. 5, 2009

(65) Prior Publication Data

US 2010/0190812 A1 Jul. 29, 2010

Related U.S. Application Data

(60) Provisional application No. 61/111,561, filed on Nov. 5, 2008, provisional application No. 61/155,789, filed on Feb. 26, 2009, provisional application No. 61/177,454, filed on May 12, 2009, provisional application No. 61/227,210, filed on Jul. 21, 2009, provisional application No. 61/240,709, filed on Sep. 9, 2009, provisional application No. 61/242,514, filed on Sep. 15, 2009, provisional application No. 61/246,799, filed on Sep. 29, 2009, provisional application No. 61/249,376, filed on Oct. 7, 2009.

(51) Int. Cl.
*A01N 43/54* (2006.01)
*A61K 31/505* (2006.01)

(52) U.S. Cl. ........................ 514/275; 544/331

(58) Field of Classification Search ............... 544/331
See application file for complete search history.

(56) References Cited

U.S. PATENT DOCUMENTS

| 7,169,791 | B2 | 1/2007 | Breitenstein et al. | |
|---|---|---|---|---|
| 2010/0016590 | A1 * | 1/2010 | Wang et al. | 544/297 |

FOREIGN PATENT DOCUMENTS

| WO | WO 2004/005281 | | 1/2004 |
|---|---|---|---|
| WO | WO 2004005281 | A1 * | 1/2004 |
| WO | WO 2005/039586 | | 5/2005 |
| WO | WO 2006/135640 | | 12/2006 |
| WO | WO 2006/135641 | | 12/2006 |
| WO | WO 2007/015870 | | 2/2007 |
| WO | WO 2007/015871 | | 2/2007 |
| WO | WO 2007/017734 | | 2/2007 |
| WO | WO 2007/018325 | | 2/2007 |
| WO | WO 2007015870 | A2 * | 2/2007 |

OTHER PUBLICATIONS

S.L. Morissette et al., Advanced Drug Delivery Reviews, 56, 275-300 (2004).*
L.D. Bighley et al., Salt Forms and Absorption, in 13 Encyclopedia of Pharmaceutical Technology 453 (M Swarbrick and J. Boylan eds., 1996).*
S. H. Neau, Pharmaceutical Salts, in Water-Insoluble Drug Formulation 417, 429 (R. Liu ed., CRC Press, 2008).*
S. Badaway et al., Salt Selection for Pharmaceutical Compounds, in Preformulation in Solid Dosage Form Dev. 63 (M. Adeyeye ed., 2008).*
R.J. Bastin et al., Salt Selection and Optimization Procedures for Pharmaceutical New Chemical Entities, 4 Organic Process Res. Dev. 427 (2000).*
P.L. Gould, Salt Selection for Basic Drugs, 33 Int. J. Therapeutics 201, 217 (1986).*
K. R. Morris et al., An Integrated Approach to the Selection of Optimal Salt Form for a New Drug Candidate, 105 Int'l. J. Pharm. 209 (1994) ("Morris").*
K. Chow et al., Engineering of Pharmaceutical Materials: an Industrial Perspective, 97 J. Pharmaceutical Sciences, 2855 (2008) ("Chow").*
A. Serajuddin, Salt Formation to Improve Solubility, 59 Adv. Drug Delivery Rev. 603 (2007).*
W-S Huang et al. "An Efficient Synthesis of Nilotinib (AMN107)" Synthesis, vol. 14, pp. 2121-2124 (2007).
"Limits of Residual Solvents" Pharmacopeial Forum, vol. 29 (4), pp. 1158-1160 (2003).

* cited by examiner

*Primary Examiner* — James O Wilson
*Assistant Examiner* — Alexander R Pagano
(74) *Attorney, Agent, or Firm* — Arent Fox LLP

(57) ABSTRACT

Crystalline forms of Nilotinib HCl are described.

28 Claims, 12 Drawing Sheets

* The peak at 28.5 corresponds to Si

* The peak at 28.5 corresponds to Si

* The peak at 28.5 corresponds to Si

* The peak at 28.5 corresponds to Si

* The peak at 28.5 corresponds to Si

* The peak at 28.5 corresponds to Si

* The peak at 28.5 corresponds to Si

* The peak at 28.5 corresponds to Si

* The peak at 28.5 corresponds to Si

* The peak at 28.5 corresponds to Si

* The peak at 28.5 corresponds to Si

* The peak at 28.5 corresponds to Si

* The peak at 28.5 corresponds to Si

* The peak at 28.5 corresponds to Si

* The peak at 28.45 corresponds to silicon powder (111).

NILOTINIB HCL CRYSTALLINE FORMS

CROSS-REFERENCE TO RELATED APPLICATIONS

This application claims the benefit of U.S. Provisional Patent Application Ser. Nos. 61/111,561, filed Nov. 5, 2008; 61/155,789, filed Feb. 26, 2009; 61/177,454, filed May 12, 2009; 61/227,210, filed Jul. 21, 2009; 61/240,709, filed Sep. 9, 2009; 61/242,514, filed Sep. 15, 2009; 61/246,799, filed Sep. 29, 2009; and 61/249,376, filed Oct. 7, 2009, which are incorporated herein by reference.

FIELD OF THE INVENTION

The present invention encompasses crystalline forms of Nilotinib HCl.

BACKGROUND OF THE INVENTION

Nilotinib, 4-methyl-N-[3-(4-methyl-1H-imidazol-1-yl)-5-(trifluoromethyl)phenyl]-3-[[4-(3-pyridinyl)-2-pyrimidinyl] amino]-benzamide, having the following formula;

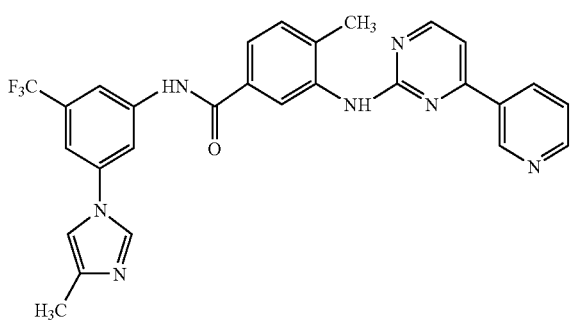

is a tyrosine kinase inhibitor used for the treatment of drug-resistant chronic myelogenous leukemia (CML), and in particular, for the treatment of chronic phase and accelerated phase Philadelphia chromosome positive chronic myeloid leukemia (CML) in adult patients whose disease has progressed on or who cannot tolerate other therapies that included imatinib. Nilotinib is administrated as a hydrochloride salt in forms of capsules that are marketed in the USA and the EU under the name Tasigna®.

PCT publications WO 2007/015870 ("WO'870") and WO 2007/015871 ("WO'871") describe several Nilotinib salts including crystalline and amorphous forms of nilotinib free base, Nilotinib hydrochloride and Nilotinib Sulfate. The crystalline forms exist in either solvate, anhydrous or hydrate forms.

The present invention relates to the solid state physical properties of Nilotinib, 4-methyl-N-[3-(4-methyl-1H-imidazol-1-yl)-5-(trifluoromethyl)phenyl]-3-[[4-(3-pyridinyl)-2-pyrimidinyl]amino]-benzamide, or of a salt thereof, or of a solid dispersion of Nilotinib HCl in a combination with pharmaceutically suitable excipient. These properties can be influenced by controlling the conditions under which 4-methyl-N-[3-(4-methyl-1H-imidazol-1-yl)-5-(trifluoromethyl)phenyl]-3-[[4-(3-pyridinyl)-2-pyrimidinyl]amino]-benzamide or a salt thereof, or of a solid dispersion of Nilotinib HCl in a combination with a pharmaceutically suitable excipient, are obtained in solid form. Solid state physical properties include, for example, the flowability of the milled solid. Flowability affects the ease with which the material is handled during processing into a pharmaceutical product. When particles of the powdered compound do not flow past each other easily, a formulation specialist must necessitate the use of glidants such as colloidal silicon dioxide, talc, starch, or tribasic calcium phosphate.

Another important solid state property of a pharmaceutical compound is its rate of dissolution in aqueous fluid. The rate of dissolution of an active ingredient in a patient's stomach fluid can have therapeutic consequences since it imposes an upper limit on the rate at which an orally administered active ingredient can reach the patient's bloodstream. The rate of dissolution is also a consideration in formulation syrups, elixirs, and other liquid medicaments. The solid state form of a compound can also affect its behavior on compaction and its storage stability.

These practical physical characteristics are influenced by the conformation and orientation of molecules in the unit cell, which define a particular polymorphic form of a substance. The polymorphic form can give rise to thermal behavior different from that of the amorphous material or another polymorphic form. Thermal behavior is measured in the laboratory by such techniques as capillary melting point, thermogravimetric analysis ("TGA"), and differential scanning calorimetry ("DSC") and can be used to distinguish some polymorphic forms from others. A particular polymorphic form can also give rise to distinct spectroscopic properties that can be detectable by powder x-ray crystallography, solid state $^{13}C$ NMR spectroscopy, and infrared spectrometry.

Generally, a crystalline solid has improved chemical and physical stability over the amorphous form, and forms with low crystallinity. Crystalline forms may also exhibit improved solubility, hygroscopicity, bulk properties, and/or flowability.

The discovery of new polymorphic forms of a pharmaceutically useful compound provides a new opportunity to improve the performance characteristics of a pharmaceutical product. It enlarges the repertoire of materials that a formulation scientist has available for designing, for example, a pharmaceutical dosage form of a drug with a targeted release profile or other desired characteristic.

There is a need in the art for new crystalline forms of nilotinib salt, specifically, HCl salt, and processes for the preparation thereof. The present invention provides new crystalline forms of Nilotinib monohydrochloride, that have favourable or improved properties such as thermal stability, dissolution, storage stability, morphology, flowability, etc.

SUMMARY OF THE INVENTION

In one embodiment, the invention encompasses a crystalline form of 4-methyl-N-[3-(4-methylimidazol-1-yl)-5-(trifluoromethyl)phenyl]-3-[(4-pyridin-3-ylpyrimidin-2-yl) amino]benzamide hydrochloride characterized by x-ray powder diffraction pattern having peaks at about 7.4, 8.9 and 20.8 degrees two theta±0.2 degrees two theta and at least two more peaks selected from the group comprising: 5.6, 10.9, 11.1, 13.8, 14.1, 21.5, 21.8 and 22.4 degrees two theta±0.2 degrees two theta, herein defined as nilotinib HCl Form T1.

In another embodiment, the present invention encompasses crystalline Nilotinib HCl, defined herein as form T1, characterized by a data selected from the group consisting of: an x-ray powder diffraction pattern having peaks at about 7.4, 8.9 and 20.8 degrees two theta±0.2 degrees two theta and at least two more peaks selected from the group consisting of: 5.6, 10.9, 11.1, 13.8, 14.1, 21.5, 21.8 and 22.4 degrees two theta±0.2 degrees two theta; and an x-ray powder diffraction pattern substantially as depicted in FIG. 1; and a combination thereof.

In yet another embodiment, the present invention encompasses crystalline Nilotinib HCl form T1 characterized by a data selected from the group consisting of: an x-ray powder diffraction pattern having peaks at about 5.6, 7.4, 8.9, 10.9 and 20.8 degrees two theta±0.2 degrees two theta; an x-ray powder diffraction pattern substantially as depicted in FIG. 2; and a combination thereof.

In one embodiment, the present invention encompasses crystalline Nilotinib HCl, defined herein as form T1, characterized by data selected from the group consisting of: an x-ray powder diffraction pattern having peaks at about 7.4, 8.9 and 20.8 degrees two theta±0.2 degrees two theta and at least two more peaks selected from the group consisting of: 5.6, 10.9, 11.1, 13.8, 14.1, 21.5, 21.8 and 22.4 degrees two theta±0.2 degrees two theta; and an x-ray powder diffraction pattern substantially as depicted in FIG. 1; an x-ray powder diffraction pattern having peaks at about 5.6, 7.4, 8.9, 10.9 and 20.8 degrees two theta±0.2 degrees two theta; an x-ray powder diffraction pattern substantially as depicted in FIG. 2; and combinations thereof.

In another embodiment, the invention also encompasses a process for preparing nilotinib HCl Form T1 by slurrying Nilotinib HCl form B in dimethyl sulfoxide ("DMSO") to obtain nilotinib HCl Form T1.

In yet another embodiment, the present invention encompasses a crystalline Nilotinib HCl, defined herein as Form T2, characterized by data selected from the group consisting of: an x-ray powder diffraction pattern having peaks at about: 7.1, 8.7, 11.5, 14.0, 15.3, 16.6, 17.4, 19.4 and 25.5±0.2 degrees two-theta, an x-ray powder diffraction pattern substantially as depicted in FIG. 3; and combinations thereof.

In another embodiment, the present invention encompasses crystalline Nilotinib HCl, defined herein as Form T3, characterized by data selected from the group consisting of: an x-ray powder diffraction pattern having peaks at about: 7.0, 8.5, 11.4, 12.1, 14.2, 17.2, 19.2, 22.1, 23.2 and 25.3±0.2 degrees two-theta; an x-ray powder diffraction pattern substantially as depicted in FIG. 4; and combinations thereof.

In one embodiment, the invention further encompasses crystalline Nilotinib HCl, defined herein as Form T4, characterized by data selected from the group consisting of: an x-ray powder diffraction pattern having peaks at about: 5.9, 8.8, 11.9, 15.3, 16.6, 19.7, 20.3, 25.4, 26.9 and 27.4±0.2 degrees two-theta; an x-ray powder diffraction pattern substantially as depicted in FIG. 5; and combinations thereof.

In yet another embodiment, the present invention encompasses crystalline Nilotinib HCl, defined herein as Form T5, characterized by data selected from the group consisting of: an x-ray powder diffraction pattern having peaks at about: 7.1, 14.0, 18.4, 20.8, 21.5, 22.5, 24.8, 25.4 and 27.3±0.2 degrees two-theta; an x-ray powder diffraction pattern substantially as depicted in FIG. 6; and combinations thereof.

In another embodiment, the present invention encompasses crystalline Nilotinib HCl, defined herein as Form T6, characterized by data selected from the group consisting of: an x-ray powder diffraction pattern having peaks at about: 7.2, 8.8, 14.4, 22.3, 23.4, 25.7, 26.4, 27.7, 29.6 and 31.5±0.2 degrees two-theta an x-ray powder diffraction pattern substantially as depicted in FIG. 7; and combinations thereof.

In yet another embodiment, the invention encompasses crystalline Nilotinib HCl, defined herein as Form T7, characterized by an x-ray powder diffraction pattern substantially as depicted in FIG. 8.

In one embodiment, the invention encompasses crystalline Nilotinib HCl, defined herein as Form T7, characterized by data selected from the group consisting of: an x-ray powder diffraction pattern having peaks at about 3.8, 7.5, 18.7, 19.9, and 25.4 degrees two theta±0.2 degrees two theta; an x-ray powder diffraction pattern substantially as depicted in FIG. 8; and a combination thereof. Nilotinib HCl Form T7 may be further characterized by x-ray powder diffraction pattern having additional peaks at about 8.7, 11.4, 15.2, 19.4 and 22.3 degrees two theta±0.2 degrees two theta.

In one embodiment, the invention encompasses crystalline Nilotinib HCl, defined herein as Form T8, characterized by an x-ray powder diffraction pattern substantially as depicted in FIG. 9.

In another embodiment, the invention encompasses crystalline Nilotinib HCl, defined herein as Form T8, characterized by data selected from the group consisting of: an x-ray powder diffraction pattern having peaks at about 6.5, 7.4, 18.3, 23.1 and 24.3 degrees two theta±0.2 degrees two theta; an x-ray powder diffraction pattern substantially as depicted in FIG. 9; and a combination thereof. Nilotinib HCl Form T8 may be further characterized by x-ray powder diffraction pattern having additional peaks at about 12.1, 13.5 and 27.2 degrees two theta±0.2 degrees two theta.

In another embodiment, the present invention encompasses crystalline Nilotinib HCl, defined herein as Form T9, characterized by data selected from the group consisting of: an x-ray powder diffraction pattern having peaks at about: 8.7, 9.4, 12.2, 17.4, 18.1, 19.4, 22.2, 24.1, 25.1, 25.8 and 26.2±0.2 degrees two-theta; an x-ray powder diffraction pattern substantially as depicted in FIG. 10; and combinations thereof.

In yet another embodiment, the present invention encompasses crystalline Nilotinib HCl, defined herein as Form T10, characterized by an x-ray powder diffraction pattern substantially as depicted in FIG. 11.

In one embodiment, the invention encompasses crystalline Nilotinib HCl, defined herein as Form T10, characterized by data selected from the group consisting of: an x-ray powder diffraction pattern having peaks at about 8.9, 14.0, 21.0, 23.8 and 25.6 degrees two theta±0.2 degrees two theta; an x-ray powder diffraction pattern substantially as depicted in FIG. 11; and a combination thereof. Nilotinib HCl Form T10 may be further characterized by x-ray powder diffraction pattern having additional peaks at about 8.0, 15.2, 16.9, 22.3 and 29.0 degrees two theta±0.2 degrees two theta.

In one embodiment, the invention encompasses crystalline Nilotinib HCl, defined herein as Form T11, characterized by data selected from the group consisting of: an x-ray powder diffraction pattern having peaks at about 7.4, 8.7, 17.4, 25.3, 26.2 and 35.1±0.2 degrees two-theta; an x-ray powder diffraction pattern substantially as depicted in FIG. 12; and combinations thereof.

In another embodiment, the present invention encompasses crystalline Nilotinib HCl, defined herein as Form T12, characterized by data selected from the group consisting of: an x-ray powder diffraction pattern having peaks at about 7.4, 9.5, 12.3, 14.8, 15.9, 19.4, 19.8, 22.3, 24.3 and 25.9±0.2 degrees two-theta an x-ray powder diffraction pattern substantially as depicted in FIG. 13.

In yet another embodiment, the present invention encompasses crystalline Nilotinib HCl, defined herein as Form T13, characterized by data selected from the group consisting of: an x-ray powder diffraction pattern having peaks at about 8.2, 12.8, 15.7, 16.5, 21.7 and 23.9±0.2 degrees two-theta; an x-ray powder diffraction substantially as depicted in FIG. 14; and combinations thereof.

In one embodiment, the invention encompasses crystalline Nilotinib HCl, defined herein as Form T14, characterized by data selected from the group consisting of: an x-ray powder diffraction pattern having peaks at about 7.5, 7.9, 8.7, 19.4 and 25.3 degrees two theta±0.2 degrees two theta; an x-ray powder diffraction pattern substantially as depicted in FIG. 15; and a combination thereof. Nilotinib HCl Form T14 may be further characterized by x-ray powder diffraction pattern having additional peaks at about 11.3, 13.4 and 17.4 degrees two theta±0.2 degrees two theta.

In another embodiment, the invention encompasses crystalline Nilotinib HCl, defined herein as Form T15, characterized by data selected from the group consisting of: an x-ray powder diffraction pattern having peaks at about 6.3, 7.3, 8.6, 12.2 and 18.2 degrees two theta±0.2 degrees two theta; an x-ray powder diffraction pattern substantially as depicted in FIG. 16; and a combination thereof. Nilotinib HCl Form T15 may be further characterized by x-ray powder diffraction pattern having additional peaks at about 23.0 and 24.3 degrees two theta±0.2 degrees two theta.

In yet another embodiment, the present invention encompasses crystalline Nilotinib HCl, defined herein as Form T16, characterized by data selected from the group consisting of: an x-ray powder diffraction pattern having peaks at about 8.1, 9.0, 14.1, 18.0 and 21.4 degrees two theta±0.2 degrees two theta; an x-ray powder diffraction pattern substantially as depicted in FIG. 17; and a combination thereof. Nilotinib HCl Form T16 may be further characterized by x-ray powder diffraction pattern having additional peaks at about 21.1, 21.8 and 22.1 degrees two theta±0.2 degrees two theta.

In one embodiment, the present invention encompasses a solid dispersion of Nilotinib HCl in a combination with a pharmaceutically suitable excipient, characterized by an x-ray powder diffractogram substantially as depicted in FIG. 18.

In another embodiment, the present invention also encompasses a process for preparing a solid dispersion of Nilotinib HCl in a combination with a pharmaceutically suitable excipient comprising dissolving Nilotinib HCl and a suitable excipient in $C_1$-$C_4$ alcohol; and removing the solvent to obtain the solid dispersion of Nilotinib HCl in a combination with a pharmaceutically suitable excipient.

In yet another embodiment, the present invention encompasses a process for preparing a solid dispersion of Nilotinib HCl in a combination with a pharmaceutically suitable excipient comprising the step of spray drying a solution comprising Nilotinib HCl and a pharmaceutically suitable excipient in $C_1$-$C_4$ alcohol, using an outlet temperature of about 35° C. to about 40° C. Preferably, the inlet temperature is 60° C. to about 70° C.

In another embodiment, the present invention encompasses a process for preparing the solid dispersion of Nilotinib HCl in a combination with a pharmaceutically suitable excipient by a process comprising: combining Nilotinib HCl with a pharmaceutically suitable excipient and a $C_1$-$C_4$ alcohol; heating to obtain a solution; and spray drying.

In another embodiment, the present invention encompasses crystalline Nilotinib HCl, defined herein as Form T17, characterized by data selected from the group consisting of: an x-ray powder diffraction pattern having peaks at about 5.7, 9.8, 15.0, 15.8 and 17.3 degrees two theta±0.2 degrees two theta; an x-ray powder diffraction pattern substantially as depicted in FIG. 19; an x-ray powder diffraction pattern substantially as depicted in FIG. 20; a solid-state $^{13}$C NMR spectrum with signals at about and 113.1, 133.1, 160.9±0.2 ppm; a solid-state $^{13}$C NMR spectrum having chemical shifts differences between the signal exhibiting the lowest chemical shift and another in the chemical shift range of 100 to 180 ppm of about 9.2, 29.2 and 57.0±0.1 ppm, wherein the signal exhibiting the lowest chemical shift in the chemical shift area of 100 to 180 ppm is typically at about 103.9±1 ppm; $^{13}$C NMR spectrum as depicted in FIG. 21; $^{13}$C NMR spectrum as depicted in FIG. 22; and combinations thereof. Nilotinib HCl Form T17 may be further characterized by x-ray powder diffraction pattern having additional peaks at about 7.5, 11.4, 18.6, 19.6 and 20.7 degrees two theta±0.2 degrees two theta or at about 7.6, 11.4, 18.7, 19.7 and 20.7 degrees two theta±0.2 degrees two theta.

In yet another embodiment, the present invention encompasses a process for preparing Nilotinib HCl Form T17 comprising:

a) combining Nilotinib base form A with absolute ethanol and HCl to obtain a slurry;
b) heating to obtain a solution;
c) cooling; and
d) drying.

Alternatively, Nilotinib HCl form T17 can be prepared by combining Nilotinib base form A with absolute ethanol and HCl to obtain a slurry. The slurry is then heated sufficiently to form a solution in which at least some of the solid material in the slurry is dissolved. The solution is then cooled sufficiently to precipitate Nilotinib HCl, which is then dried sufficiently to form Nilotinib HCl form T17.

In one embodiment, the present invention further comprises another process for preparing Nilotinib HCl form T17 comprising: combining Nilotinib HCl amorphous form with acetone or tetrafydrofuran (THF) to obtain a slurry; agitating the slurry; and drying the slurry to obtain Nilotinib HCl form T17.

In another embodiment, the present invention comprises a process for preparing a mixture of Nilotinib HCl form T17 and nilotinib HCl form A comprising: combining Nilotinib HCl amorphous form with isopropyl acetate or ethyl acetate to obtain a slurry; agitating the slurry; and drying to obtain a mixture of Nilotinib HCl form T17 and Nilotinib HCl form A.

In yet another embodiment, the present invention provides a process for preparing Nilotinib HCl form T17 comprising: slurrying a mixture of Nilotinib HCl form A and Nilotinib HCl for T17 with IPA or acetonitrile to obtain Nilotinib HCl form T17.

In one embodiment, the present invention encompasses crystalline Nilotinib HCl, defined herein as Form T18, characterized by data selected from the group consisting of: an x-ray powder diffraction pattern having peaks at about 5.5, 7.2, 8.7, 9.6 and 10.9 degrees two theta±0.2 degrees two theta; an x-ray powder diffraction pattern having peaks at about 5.5, 7.1, 8.7, 9.6 and 10.9 degrees two theta±0.2 degrees two theta an x-ray powder diffraction pattern substantially as depicted in FIG. 23; and a combination thereof. Nilotinib HCl Form T18 may be further characterized by x-ray powder diffraction pattern having additional peaks at about 14.4, 17.0, 19.2, 21.9 and 22.3 degrees two theta±0.2 degrees two theta or at about 14.4, 17.0, 19.2, 21.9 and 22.4 degrees two theta±0.2 degrees two theta.

In one embodiment, the present invention also encompasses a process for preparing Nilotinib HCl Form T18 comprising:

a) combining Nilotinib base form A with absolute ethanol and HCl to obtain a slurry;
b) heating; and
c) cooling to form Nilotinib HCl Form T18.

In yet another embodiment, the present invention provides a process for preparing Nilotinib HCl Form T17 by drying Nilotinib HCl Form T18.

In one embodiment, the present invention provides another process for preparing Nilotinib HCl Form T18 comprising: slurrying a mixture of Nilotinib HCl form A and Nilotinib HCl form T17 in ethanol at a temperature of about 55° C. to about 78° C.

In another embodiment, the present invention provides additional process for preparing Nilotinib HCl form T18 comprising: combining Nilotinib HCl form T17 with absolute ethanol; heating; and cooling to obtain Nilotinib HCl form T18.

In another embodiment, the present invention encompasses crystalline Nilotinib HCl, defined herein as Form T19, characterized by data selected from the group consisting of: an x-ray powder diffraction pattern having peaks at about 5.5, 7.2, 9.2, 9.6 and 10.9 degrees two theta±0.2 degrees two theta; an x-ray powder diffraction pattern substantially as depicted in FIG. 24; and a combination thereof. Nilotinib HCl Form T19 may be further characterized by x-ray powder diffraction pattern having additional peaks at about 14.1, 14.9, 17.7, 18.5 and 19.3 degrees two theta±0.2 degrees two theta.

In yet another embodiment, the present invention provides a process for preparing Nilotinib HCl Form T19 comprising: slurrying Nilotinib HCl form B in ethanol; heating; and cooling.

In one embodiment the present invention provides a pharmaceutical composition comprising any one, or combination, of a solid dispersion of Nilotinib HCl in a combination with a pharmaceutically suitable excipient and/or crystalline Forms T1-T19, described above and at least one additional pharmaceutically acceptable excipient.

DETAILED DESCRIPTION OF THE INVENTION

Figure 1:
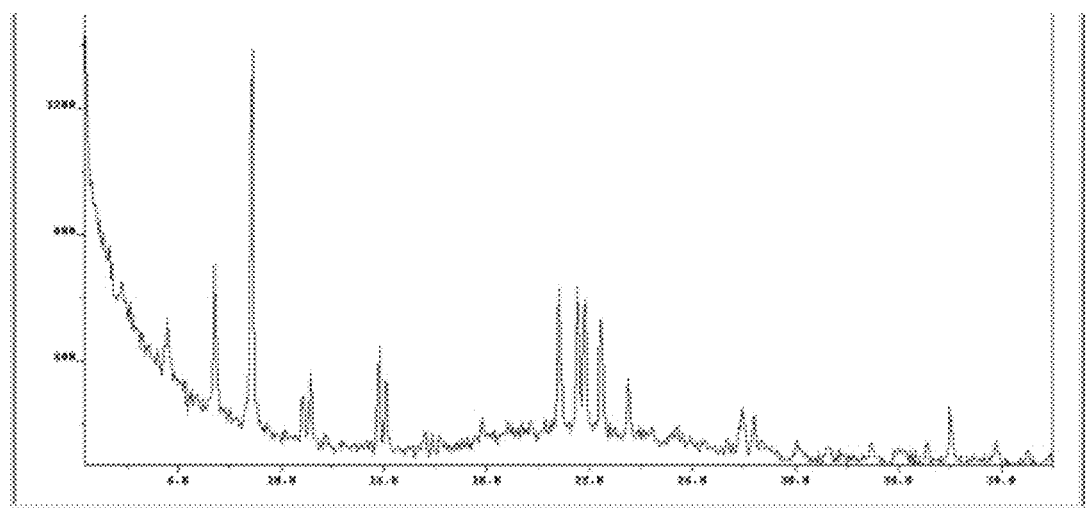
FIG. 1 illustrates a characteristic x-ray powder diffractogram of nilotinib HCl Form T1.

As used herein, the terms "room temperature" or "ambient temperature" refers to a temperature of about 15° C. to about 30° C., more preferably, to a temperature of about 20° C. to about 25° C.

As used herein, the term "overnight" refers to about 13 hours to about 24 hours, more preferably, to about 16 hours to about 24 hours.

As used herein, the term "spray drying" broadly refers to processes involving breaking up liquid mixtures into small droplets (atomization), and rapidly removing solvent from the mixture. In a typical spray drying apparatus, there is a strong driving force for evaporation of solvent from the droplets, which may be provided by providing a drying gas. Spray drying processes and equipment are described in Perry's Chemical Engineer's Handbook, pgs. 20-54 to 20-57 (Sixth Edition 1984), which is incorporated herein by reference.

By way of a non-limiting example only, the typical spray drying apparatus comprises a drying chamber, atomizing means for atomizing a solvent-containing feed into the drying chamber, a source of drying gas that flows into the drying chamber to remove solvent from the atomized-solvent-containing feed, an outlet for the products of drying, and product collection means located downstream of the drying chamber. Examples of such apparatuses include Niro Models PSD-1, PSD-2 and PSD-4 (Niro A/S, Soeborg, Denmark), and BUCHI Model B-191 mini spray dryer. Commercial equipment for spray drying may be used, such as model AGM-2M-SD by the manufacturer Hosokawa Micron Corporation.

As used herein, an "inlet temperature" is the temperature at which the solution enters the spray dryer; an "outlet temperature" is the temperature at which the gas exits the spray dryer.

Inlet or outlet temperatures may be varied, if necessary, depending on the equipment, gas, or other experimental parameters. For example, it is known that the outlet temperature may depend on parameters such as aspirator rate, air humidity, inlet temperature, spray air flow, feed rate, or concentration. The person skilled in the art would know how to vary these parameters to obtain the desired outlet temperature.

Typically, the product collection means includes a cyclone connected to the drying apparatus. In the cyclone, the particles produced during spray drying are separated from the drying gas and evaporated solvent, allowing the particles to be collected. A filter may also be used to separate and collect the particles produced by spray drying. Spray-drying may be performed in a conventional manner in the processes of the present invention (see, e.g., Remington: The Science and Practice of Pharmacy, 19th ed., vol. II, pg. 1627, herein incorporated by reference). The drying gas used in the invention may be any suitable gas, although inert gases such as nitrogen, nitrogen-enriched air, and argon are preferred. Nitrogen gas is a particularly preferred drying gas for use in the process of the invention.

As used herein, the term "solid dispersion" refers to a resultant single phase or more upon distribution of two compounds in each other.

As used herein, the term "reduced pressure" refers to a pressure of about 10 mbar to about 50 mbar, more preferably, a pressure of about 20 mbar to about 30 mbar.

As used herein, the term "absolute ethanol" refers to ethanol having 1% (weight/weight percentage) or less of water, preferably, 0.5% or less of water, more preferably, 0.25% or less of water, most preferably, 0.15% or less of water.

As used herein, the term "slurry" refers to a heterogeneous mixture of solid(s) and liquid(s).

As used herein, the term "anhydrous" refers to a crystalline form having less than about 2% total water by weight (bound and unbound).

As used herein, the term "pure" refers to Nilotinib HCl crystalline Form having about 10% w/w, or less, of Nilotinib HCl form A. In preferred embodiments, a pure Nilotinib HCl crystalline form contains about 10% w/w, or less, of any other crystalline form of Nilotinib HCl; i.e., there is no other crystalline form present in an amount exceeding about 10%. As used herein the term "dry" in relation to acetone, THF, isopropyl acetate and ethyl acetate relates to a solvent, which was dried over 4 A molecular sieves prior to use.

As used herein, the term "agitating" refers to any means of enhancing mixing, such as shaking or stirring.

PCT publication no. WO 2007/015870 ("WO'870") describes crystalline forms of nilotinib including crystalline forms A and B. Form A is characterized by an X-ray powder diffraction pattern having at least one, more preferably at least two, still more preferably at least four and most preferably all maxima selected from about 8.5, 11.0, 11.5, 17.2, 18.8, 19.2, 20.8, 22.1 and 26.0 degrees two theta±0.2 degrees two theta. Form B is characterized by an X-ray powder diffraction pattern having at least one, more preferably at least two, still more preferably at least four and most preferably all maxima selected from about 7.2, 9.2, 11.4, 12.0, 12.3, 14.6, 14.8, 15.7, 17.6, 19.2, 19.5, 20.5, 22.0, 23.4, 23.9, 25.0, 25.5, 25.9, 27.0 degrees two theta±0.2 degrees two theta.

The present invention addresses a need in the art by providing new crystalline forms of Nilotinib HCl.

Figure 2:
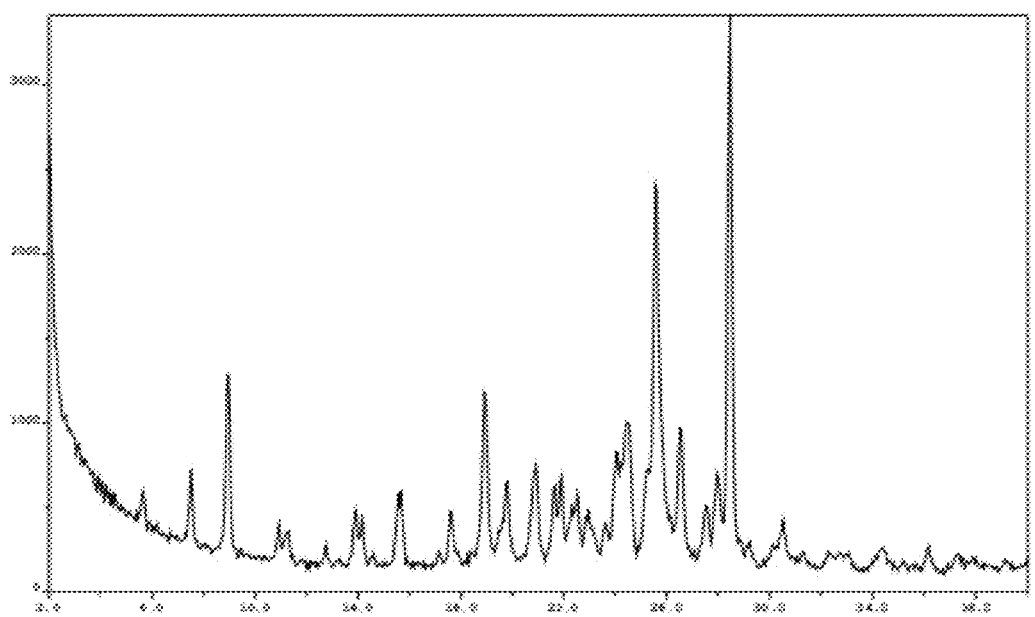
FIG. 2 illustrates a characteristic x-ray powder diffractogram of nilotinib HCl Form T1.

The present invention encompasses crystalline Nilotinib HCl, defined herein as form T1, characterized by data selected from the group consisting of: an x-ray powder diffraction pattern having peaks at about 7.4, 8.9 and 20.8 degrees two theta±0.2 degrees two theta and at least two more peaks selected from the group consisting of: 5.6, 10.9, 11.1, 13.8, 14.1, 21.5, 21.8 and 22.4 degrees two theta±0.2 degrees two theta; and an x-ray powder diffraction pattern substantially as depicted in FIG. 1; an x-ray powder diffraction pattern having peaks at about 5.6, 7.4, 8.9, 10.9 and 20.8 degrees two theta±0.2 degrees two theta; an x-ray powder diffraction pattern substantially as depicted in FIG. 2; and combinations thereof. Nilotinib HCl Form T1 may be further characterized by x-ray powder diffraction pattern having additional peaks at about 11.4, 13.8, 14.1, 21.5 and 21.8 degrees two theta±0.2 degrees two theta.

Optionally, Nilotinib HCl Form T1 is characterized by x-ray powder diffraction pattern having peaks at about 7.4, 8.9, 10.9, 20.8 and 21.5 degrees two theta±0.2 degrees two theta or by x-ray powder diffraction pattern having peaks at about 7.4, 8.9, 11.1, 13.8 and 20.8 degrees two theta±0.2 degrees two theta.

Typically, Nilotinib HCl crystalline form T1 is a DMSO solvate.

Unlike Nilotinib HCl form B, which is not soluble in IPA, as described in WO '870, Nilotinib HCl form T1 is soluble in IPA at reflux.

The invention also encompasses a process for preparing nilotinib HCl Form T1 by slurrying Nilotinib HCl form B in dimethyl sulfoxide ("DMSO") to obtain nilotinib HCl Form T1.

Preferably, the DMSO contains water, more preferably, the water content is about 0.01% to about 0.04%.

Preferably, the suspension is stirred until a precipitate of Form T1 is obtained. Preferably, the stirring is at about 350 rpm to about 700 rpm, more preferably, at about 700 rpm. Preferably, the stirring is at about room temperature, more preferably at about 25° C. Preferably, the stirring is done for about 16 hours to about 25 hours, more preferably, for about 24 hours.

The precipitate may be further isolated. The isolation may be done by filtering. Preferably, the filtering occurs under reduced pressure, such as at about 0 mbar to about 40 mbar, preferably, at about 3.5 mbar.

Figure 3:
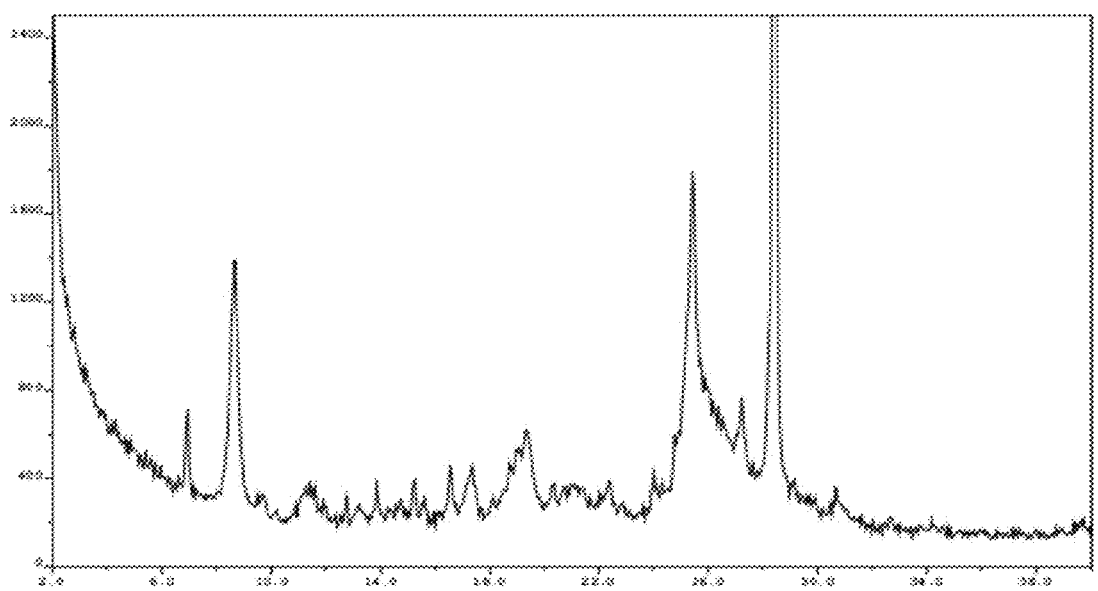
FIG. 3 illustrates a characteristic x-ray powder diffractogram of nilotinib HCl Form T2.

The present invention encompasses crystalline Nilotinib HCl Form T2 characterized by data selected from the group consisting of: an x-ray powder diffraction pattern having peaks at about: 7.1, 8.7, 11.5, 14.0, 15.3, 16.6, 17.4, 19.4 and 25.5±0.2 degrees two-theta, an x-ray powder diffraction pattern substantially as depicted in FIG. 3; and combinations thereof.

The present invention also encompasses a process for preparing nilotinib HCl Form T2 by suspending nilotinib base form A in absolute ethanol or in iso-propanol (IPA); and adding HCl dissolved in IPA without heating, to obtain a precipitate.

Nilotinib base form A may be prepared according to U.S. Pat. No. 7,169,791, which is incorporated herein by reference.

Preferably, the HCl in IPA is at a concentration of about 19.48%.

After the HCl addition, a slurry is obtained. Preferably, the slurry is stirred to obtain the precipitate. Preferably, stirring is at about room temperature. Preferably, stirring is done for about 16 hours to about 24 hours, more preferably, for about 16 hours.

The precipitate is further isolated. The isolation may be done by filtration. The isolated precipitate may be further washed and dried. Preferably, washing is done with the same solvent used in the process. Preferably, washing is done twice. Preferably, the drying is done using vacuum oven, more preferably, the drying is at a temperature of about 50° C. to about 60° C., most preferably, the drying is at a temperature of about 50° C. Preferably, the drying is overnight.

Figure 4:
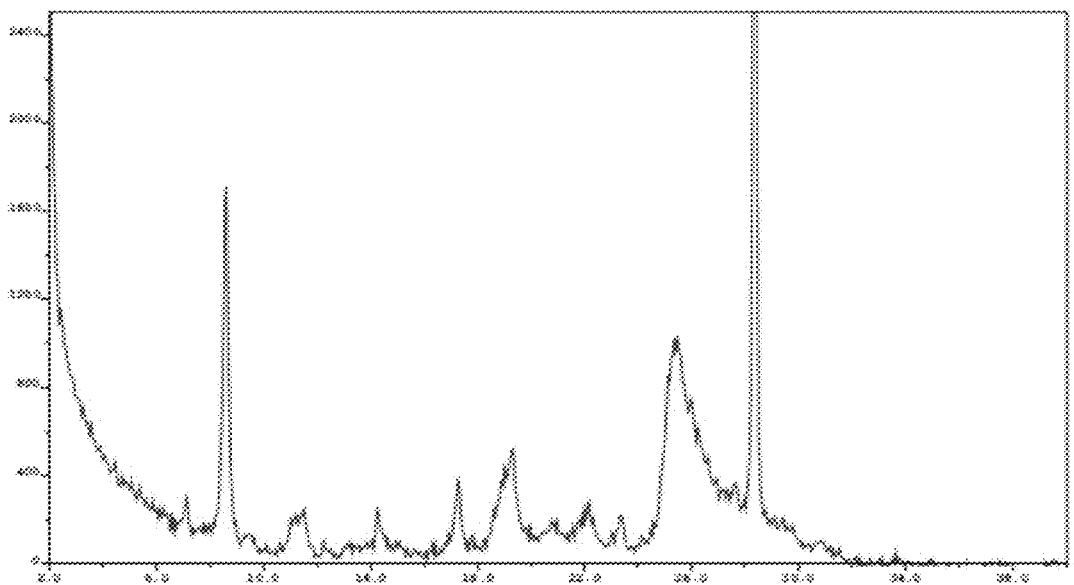
FIG. 4 illustrates a characteristic x-ray powder diffractogram of nilotinib HCl Form T3.

The present invention encompasses crystalline Nilotinib HCl, defined herein as Form T3, characterized by data selected from the group consisting of: an x-ray powder diffraction pattern having peaks at about: 7.0, 8.5, 11.4, 12.1, 14.2, 17.2, 19.2, 22.1, 23.2 and 25.3±0.2 degrees two-theta; an x-ray powder diffraction pattern substantially as depicted in FIG. 4; and combinations thereof.

The invention also encompasses a process for preparing nilotinib HCl Form T3 by suspending nilotinib base form A in ethanol 95%; and adding HCl dissolved in IPA without heating, to obtain a precipitate.

Preferably, the HCl in IPA is at a concentration of about 19.48%.

After the HCl addition, a slurry is obtained. Preferably, the slurry is stirred to obtain the precipitate. Preferably, the stirring is at about room temperature. Preferably, the stirring is done for about 16 hours to about 24 hours, more preferably, for about 16 hours.

The precipitate may be further isolated. The isolation may be done by filtration. The isolated precipitate may be further washed and dried. Preferably, washing is done with ethanol 95%. Preferably, washing is done twice. Preferably, the drying is done using vacuum oven, more preferably, the drying is at a temperature of about 50° C. to about 60° C., most preferably, the drying is at a temperature of about 50° C. Preferably, the drying is done overnight.

Figure 5:
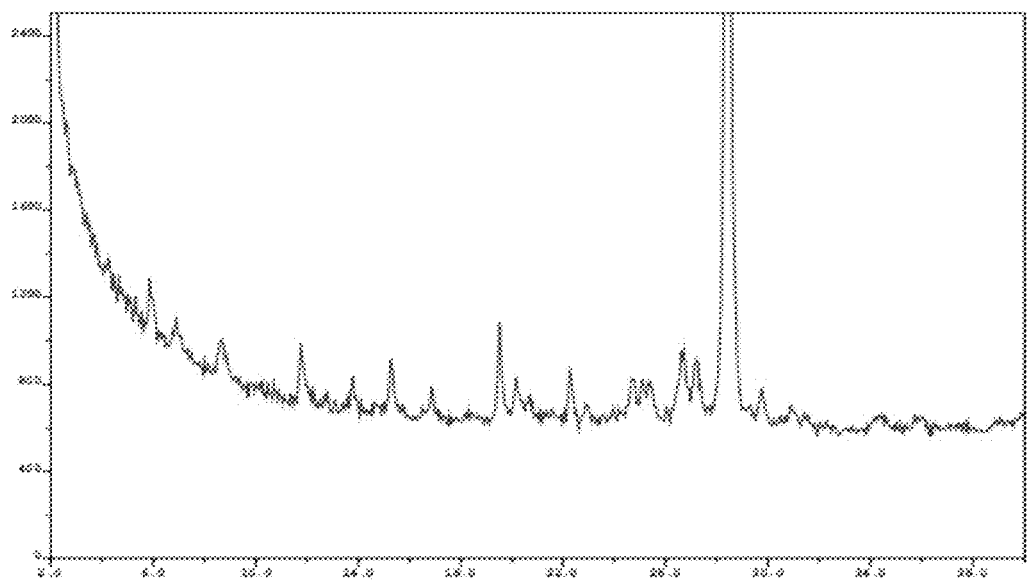
FIG. 5 illustrates a characteristic x-ray powder diffractogram of nilotinib HCl Form T4.

The invention further encompasses crystalline Nilotinib HCl, defined herein as Form T4, characterized by data selected from the group consisting of: an x-ray powder diffraction pattern having peaks at about: 5.9, 8.8, 11.9, 15.3, 16.6, 19.7, 20.3, 25.4, 26.9 and 27.4±0.2 degrees two-theta; an x-ray powder diffraction pattern substantially as depicted in FIG. 5; and combinations thereof.

The invention also provides a process for preparing nilotinib HCl Form T4 by suspending nilotinib base form A in 1-propanol; and adding HCl dissolved in IPA to obtain a precipitate.

Preferably, the HCl in IPA is at a concentration of about 19.48%.

After the HCl addition, a slurry is obtained. Preferably, the slurry is stirred to obtain the precipitate. Preferably, stirring is at about room temperature. Preferably, stirring is done for about 16 hours to about 24 hours, more preferably, for about 16 hours.

The precipitate may be further isolated. The isolation may be done by filtration. The isolated precipitate may be further washed and dried. Preferably, washing is done with 1-propanol. Preferably, washing is done twice. Preferably, the drying is done using vacuum oven, more preferably, the drying is at a temperature of about 50° C. to about 60° C., most preferably, the drying is at a temperature of about 50° C. Preferably, the drying is done overnight.

Figure 6:
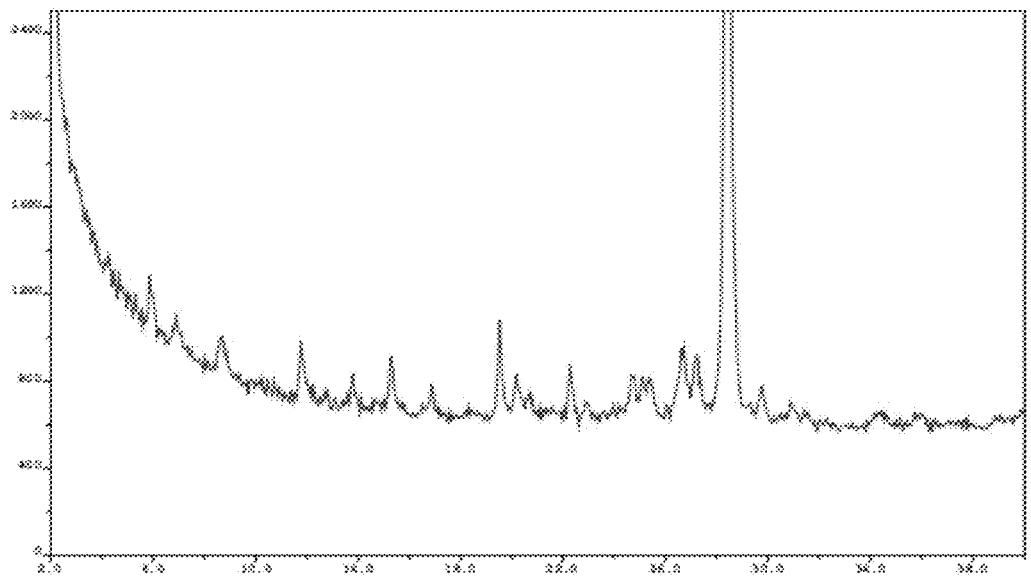
FIG. 6 illustrates a characteristic x-ray powder diffractogram of nilotinib HCl Form T5.

The present invention encompasses crystalline Nilotinib HCl, defined herein as Form T5, characterized by data selected from the group consisting of: an x-ray powder diffraction pattern having peaks at about: 7.1, 14.0, 18.4, 20.8, 21.5, 22.5, 24.8, 25.4 and 27.3±0.2 degrees two-theta; an x-ray powder diffraction pattern substantially as depicted in FIG. 6; and combinations thereof.

The invention also encompasses a process for preparing nilotinib HCl Form T5 by suspending nilotinib base form A in n-butanol; and adding HCl dissolved in IPA, to obtain a precipitate.

Preferably, the HCl in IPA is at a concentration of about 19.48%.

After the HCl addition, a slurry is obtained. Preferably, the slurry is stirred to obtain the precipitate. Preferably, stirring is at about room temperature. Preferably, stirring is done for about 16 hours to about 24 hours, more preferably, for about 16 hours.

The precipitate is further isolated. The isolation may be done by filtration. The isolated precipitate may be further washed and dried. Preferably, washing is done with n-butanol. Preferably, washing is done twice. Preferably, the drying is done using vacuum oven, more preferably, the drying is at a temperature of about 50° C. to about 60° C., most preferably, the drying is at a temperature of about 50° C. Preferably, the drying is done overnight.

Figure 7:
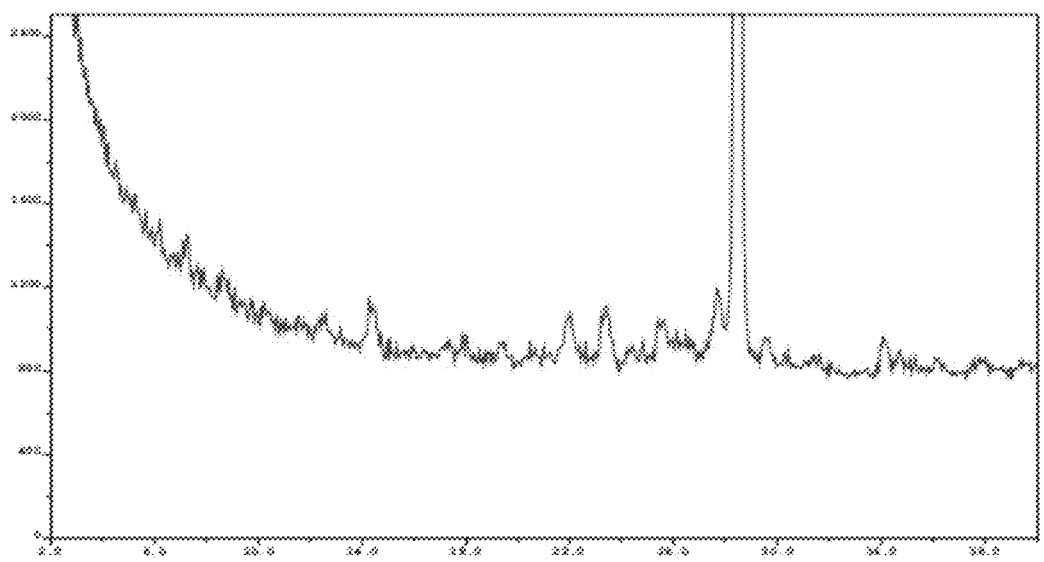
FIG. 7 illustrates a characteristic x-ray powder diffractogram of nilotinib HCl Form T6.

The present invention encompasses crystalline Nilotinib HCl, defined herein as Form T6, characterized by data selected from the group consisting of: an x-ray powder diffraction pattern having peaks at about: 7.2, 8.8, 14.4, 22.3, 23.4, 25.7, 26.4, 27.7, 29.6 and 31.5±0.2 degrees two-theta an x-ray powder diffraction pattern substantially as depicted in FIG. 7; and combinations thereof.

The invention further provides a process for preparing nilotinib HCl Form T6 by suspending nilotinib base form A in a solvent selected from the group consisting of: 2-butanol, tert-butanol and 2-pentanol; and adding HCl dissolved in IPA to obtain a precipitate.

Preferably, the HCl in IPA is at a concentration of about 19.48%.

After the HCl addition, a slurry is obtained. Preferably, the slurry is stirred to obtain the precipitate. Preferably, stirring is at about room temperature. Preferably, stirring is done for about 16 hours to about 24 hours, more preferably, for about 16 hours.

The precipitate is further isolated. The isolation may be done by filtration. The isolated precipitate may be further washed and dried. Preferably, washing is done with the same solvent used in the process. Preferably, washing is done twice. Preferably, the drying is done using vacuum oven, more preferably, the drying is at a temperature of about 50° C. to about 60° C., most preferably, the drying is at a temperature of about 50° C. Preferably, the drying is done overnight.

Figure 8:
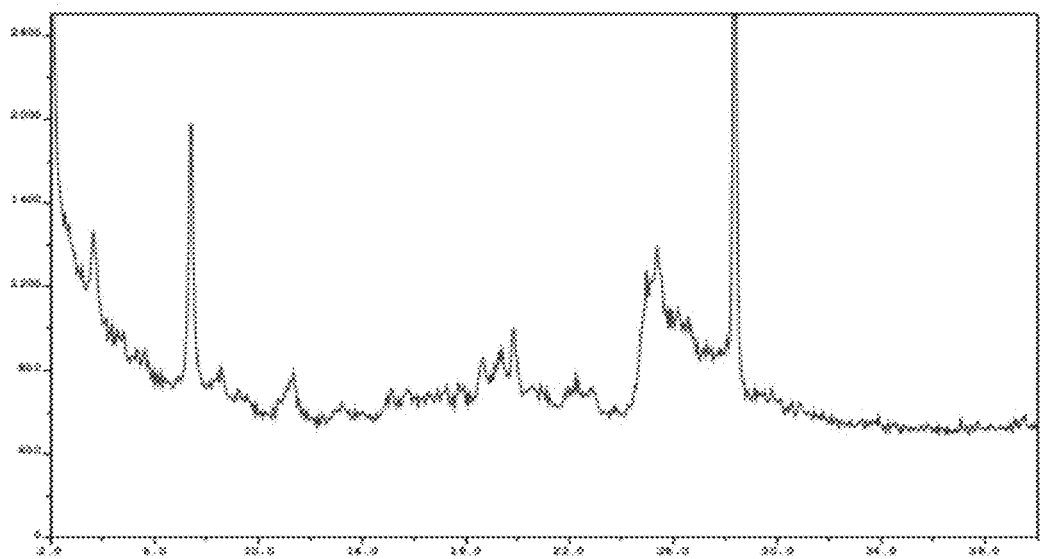
FIG. 8 illustrates a characteristic x-ray powder diffractogram of nilotinib HCl Form T7.

The invention encompasses crystalline Nilotinib HCl, defined herein as Form T7, characterized by an x-ray powder diffraction pattern substantially as depicted in FIG. 8.

Alternatively, Nilotinib HCl Form T7 is characterized by data selected from the group consisting of: an x-ray powder diffraction pattern having peaks at about 3.8, 7.5, 18.7, 19.9, and 25.4 degrees two theta±0.2 degrees two theta; an x-ray powder diffraction pattern substantially as depicted in FIG. 8; and combinations thereof. Nilotinib HCl Form T7 may be further characterized by x-ray powder diffraction pattern having additional peaks at about 8.7, 11.4, 15.2, 19.4 and 22.3 degrees two theta±0.2 degrees two theta.

The invention also encompasses a process for preparing nilotinib HCl Form T7 by a process comprising: combining nilotinib HCl Form B with benzyl alcohol to obtain a precipitate.

The combination of Nilotinib HCl form T7 with benzyl alcohol results in a slurry from which the crystalline form T7 is obtained.

Preferably, the combination of nilotinib HCl Form B and benzyl alcohol is stirred. Preferably, stirring is at about ambient temperature. Preferably, stirring is done for about 16 hours to about 24 hours, more preferably, for about 24 hours.

The precipitate is further isolated. The isolation may be done by filtration. Preferably, filtration is done on buchner. The isolated precipitate may be further dried. Preferably, drying is at a temperature of about 50° C. to about 60° C., more preferably, drying is at a temperature of about 50° C. Preferably, the drying is done under vacuum. Preferably, the drying is done overnight.

Figure 9:
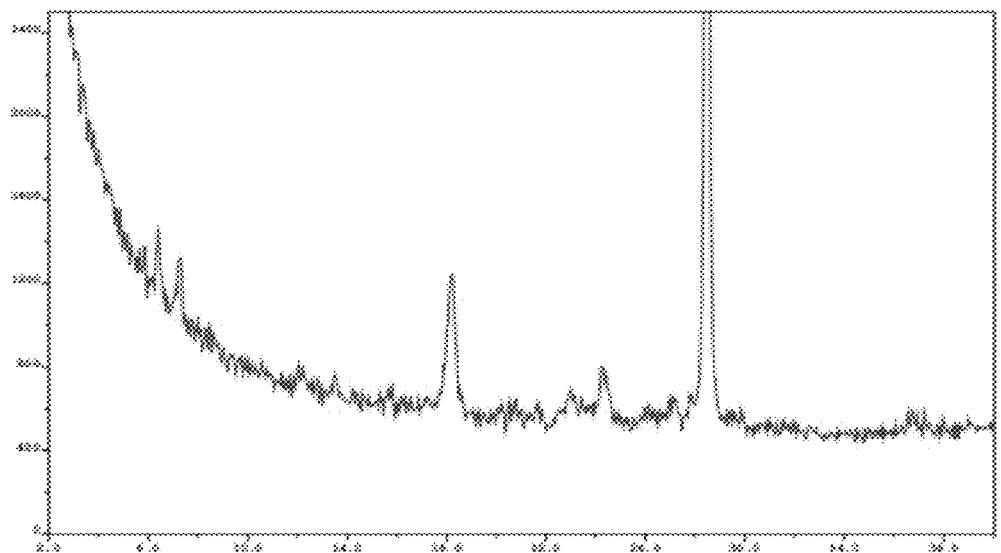
FIG. 9 illustrates a characteristic x-ray powder diffractogram of nilotinib HCl Form T8.

The invention encompasses crystalline Nilotinib HCl, defined herein as Form T8, characterized by an x-ray powder diffraction pattern substantially as depicted in FIG. 9.

Alternatively, Nilotinib HCl Form T8 is characterized by data selected from the group consisting of: an x-ray powder diffraction pattern having peaks at about 6.5, 7.4, 18.3, 23.1 and 24.3 degrees two theta±0.2 degrees two theta; an x-ray powder diffraction pattern substantially as depicted in FIG. 9; and combinations thereof. Nilotinib HCl Form T8 may be further characterized by x-ray powder diffraction pattern having additional peaks at about 12.1, 13.5 and 27.2 degrees two theta±0.2 degrees two theta.

The invention also encompasses a process for preparing Nilotinib HCl form T8 by a process comprising: combining nilotinib HCl Form B with di-methylacetamide ("DMA") to obtain a precipitate.

The combination of Nilotinib HCl form T8 with DMA results in a slurry from which the crystalline form T8 is obtained.

Preferably, the combination of nilotinib HCl Form B and DMA is stirred. Preferably, stirring is at about ambient temperature. Preferably, stirring is done for about 16 hours to about 24 hours, more preferably, for about 24 hours.

The precipitate is further isolated. The isolation may be done by filtration. Preferably, filtration is done on buchner. The isolated precipitate may be further dried. Preferably, drying is at a temperature of about 50° C. to about 60° C., more preferably, drying is at a temperature of about 50° C. Preferably, the drying is done under vacuum. Preferably, the drying is done overnight.

Figure 10:
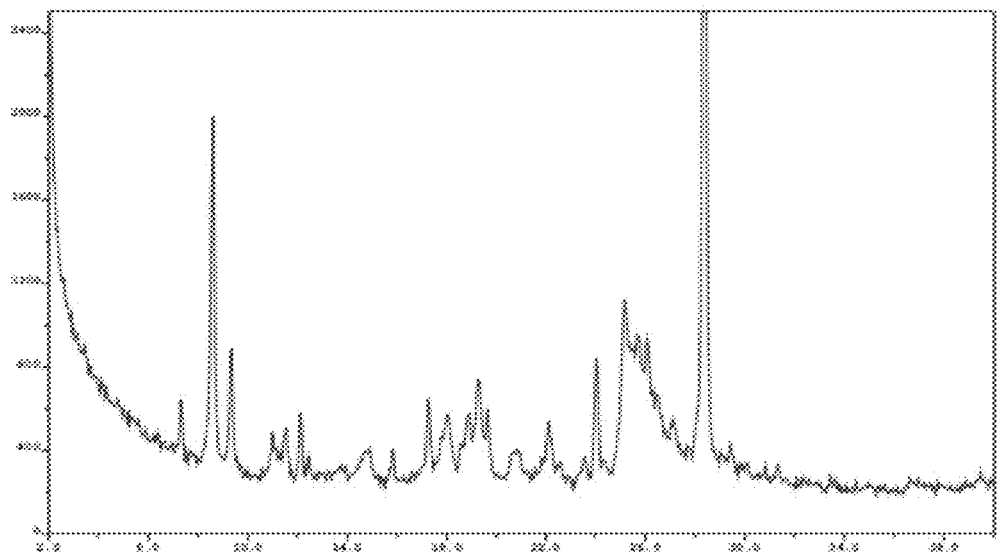
FIG. 10 illustrates a characteristic x-ray powder diffractogram of nilotinib HCl Form T9.

The present invention encompasses crystalline Nilotinib HCl, defined herein as Form T9, characterized by data selected from the group consisting of: an x-ray powder diffraction pattern having peaks at about: 8.7, 9.4, 12.2, 17.4, 18.1, 19.4, 22.2, 24.1, 25.1, 25.8 and 26.2±0.2 degrees two-theta; an x-ray powder diffraction pattern substantially as depicted in FIG. 10; and combinations thereof.

The invention further encompasses a process for preparing nilotinib HCl Form T9 by a process comprising: combining nilotinib HCl Form B with chlorobenzene to obtain a precipitate.

The combination of Nilotinib HCl form T9 with chlorobenzene results in a slurry from which the crystalline form T9 is obtained.

Preferably, the combination of nilotinib HCl Form B and chlorobenzene is stirred. Preferably, stirring is at about ambient temperature. Preferably, stirring is done for about 16 hours to about 24 hours, more preferably, for about 24 hours.

The precipitate is further isolated. The isolation may be done by filtration. Preferably, filtration is done on buchner. The isolated precipitate may be further dried. Preferably, drying is at a temperature of about 50° C. to about 60° C., more preferably, drying is at a temperature of about 50° C. Preferably, the drying is done under vacuum. Preferably, drying is done overnight.

Figure 11:
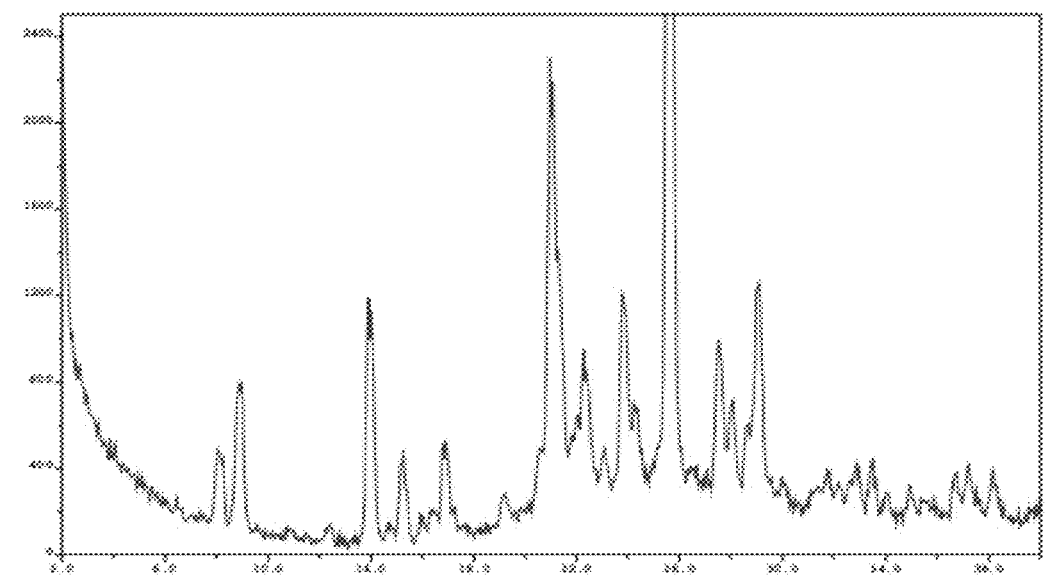
FIG. 11 illustrates a characteristic x-ray powder diffractogram of nilotinib HCl Form T10.

The present invention encompasses crystalline Nilotinib HCl, defined herein as Form T10, characterized by an x-ray powder diffraction pattern substantially as depicted in FIG. 11.

Alternatively, Nilotinib HCl Form T10 is characterized by data selected from the group consisting of: an x-ray powder diffraction pattern having peaks at about 8.9, 14.0, 21.0, 23.8 and 25.6 degrees two theta±0.2 degrees two theta; an x-ray powder diffraction pattern substantially as depicted in FIG. 11; and combinations thereof. Nilotinib HCl Form T10 may be further characterized by x-ray powder diffraction pattern having additional peaks at about 8.0, 15.2, 16.9, 22.3 and 29.0 degrees two theta±0.2 degrees two theta.

The invention further encompasses a process for preparing nilotinib HCl Form T10 a process comprising: combining nilotinib HCl Form B with ethylene glycol to obtain a precipitate.

The combination of Nilotinib HCl form T10 with ethylene glycol results in a slurry from which the crystalline form T10 is obtained.

Preferably, the combination of the nilotinib HCl Form B and ethylene glycol is stirred. Preferably, the stirring is at about ambient temperature. Preferably, the stirring is done for about 16 hours to about 24 hours, more preferably, for about 24 hours.

The precipitate is further isolated. The isolation may be done by filtration. Preferably, the filtration is done on buchner. The isolated precipitate may be further dried. Preferably, drying is at a temperature of about 50° C. to about 60° C., more preferably, drying is at a temperature of about 50° C. Preferably, the drying is done under vacuum. Preferably, drying is done overnight.

Figure 12:
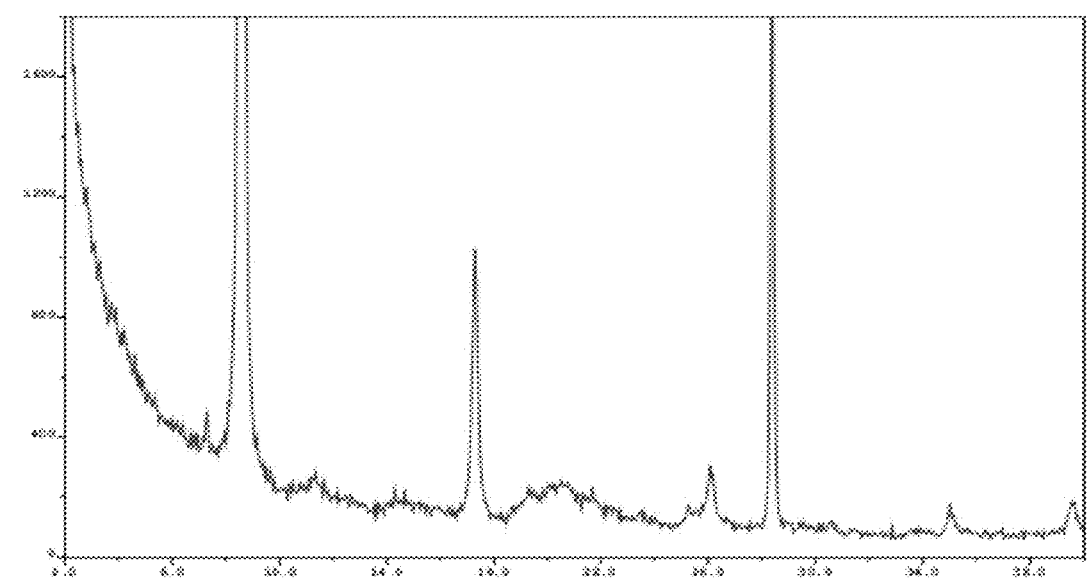
FIG. 12 illustrates a characteristic x-ray powder diffractogram of nilotinib HCl Form T11.

The invention encompasses crystalline Nilotinib HCl, defined herein as Form T11, characterized by data selected from the group consisting of: an x-ray powder diffraction pattern having peaks at about 7.4, 8.7, 17.4, 25.3, 26.2 and 35.1±0.2 degrees two-theta; an x-ray powder diffraction pattern substantially as depicted in FIG. 12; and combinations thereof.

The invention further encompasses a process for preparing nilotinib HCl Form T11 comprising combining nilotinib HCl Form B with 1-propanol; cooling; heating; and cooling to obtain a precipitate.

Preferably, the cooling is to a temperature of about −5° C. to about +5° C., more preferably, to about 0° C. Preferably, the heating is to a temperature of about 60° C. to about 70° C., more preferably, to about 65° C. Preferably, the heating rate is of about 0.1 deg/min. Preferably, the cooling rate after the heating step is of about 0.1 deg/min. Preferably, the obtained precipitate is further maintained at a temperature of about −5° C. to about +5° C. Preferably, at about 0° C. Preferably, the maintaining step is for about 1 day to about 5 days, more preferably, for about 3 days. Preferably, the maintaining step is done while stirring.

The precipitate is further isolated. The isolation may be done by filtration.

Figure 13:
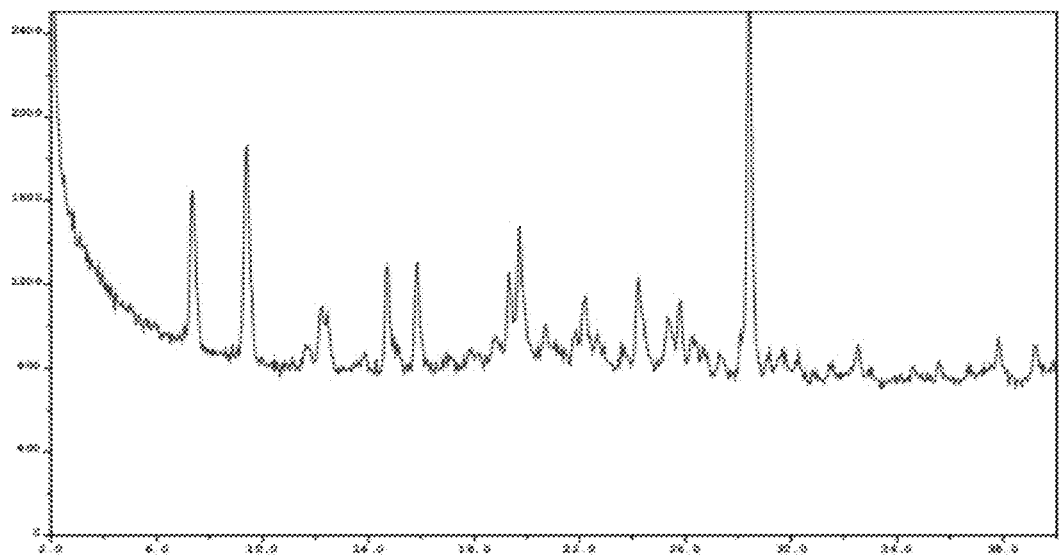
FIG. 13 illustrates a characteristic x-ray powder diffractogram of nilotinib HCl Form T12.

The present invention encompasses crystalline Nilotinib HCl, defined herein as Form T12, characterized by data selected from the group consisting of: an x-ray powder diffraction pattern having peaks at about 7.4, 9.5, 12.3, 14.8, 15.9, 19.4, 19.8, 22.3, 24.3 and 25.9±0.2 degrees two-theta an x-ray powder diffraction pattern substantially as depicted in FIG. 13.

The invention further encompasses a process for preparing nilotinib HCl Form T12 by a process comprising: combining nilotinib HCl Form B with butyl lactate; cooling; heating; and cooling to obtain a precipitate.

The combination of Nilotinib HCl form T12 with butyl acetate results in a slurry from which the crystalline form T12 is obtained.

Preferably, the cooling is to a temperature of about −5° C. to about 5° C., more preferably, to about 0° C. Preferably, the heating is from a temperature of about 70° C. to about 80° C., more preferably, to about 78° C. Preferably, the heating rate is of about 0.1 deg/min. Preferably, the cooling rate after the heating is of about 0.1 deg/min. Preferably, the obtained precipitate is further maintained at a temperature of about 0° C. Preferably, the maintaining step is for about 2 days.

The precipitate is further isolated. The isolation may be done by filtration.

Figure 14:
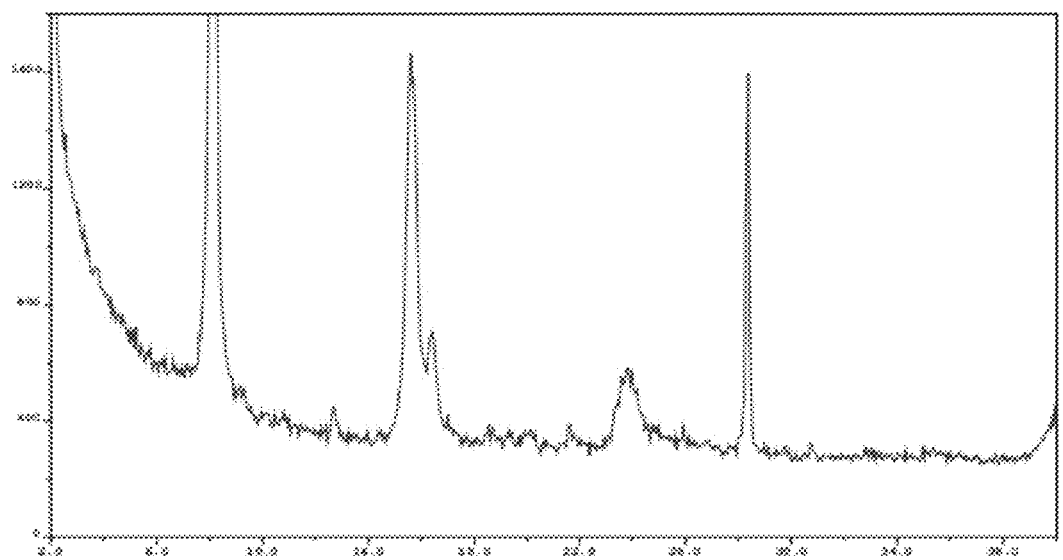
FIG. 14 illustrates a characteristic x-ray powder diffractogram of nilotinib HCl Form T13.

The present invention encompasses crystalline Nilotinib HCl, defined herein as Form T13, characterized by data selected from the group consisting of: an x-ray powder diffraction pattern having peaks at about 8.2, 12.8, 15.7, 16.5, 21.7 and 23.9±0.2 degrees two-theta; an x-ray powder diffraction substantially as depicted in FIG. 14; and combinations thereof.

The invention further encompasses a process for preparing nilotinib HCl Form T13 by a process comprising combining nilotinib HCl Form B with absolute ethanol; cooling to a temperature of about −5° C. to about +5° C.; heating; and cooling to obtain a precipitate Preferably, the cooling is to a temperature of about −5° C. to about +5° C., more preferably, to about 0° C. Preferably, the heating is to a temperature of about 70° C. to about 80° C., more preferably, of about 75° C. Preferably, the heating rate is of about 2 deg/min. Preferably, after the heating and prior to cooling, a maintaining step is performed. Preferably, the maintaining is at a temperature of about 70° C. to about 80° C., more preferably, at about 75° C. Preferably, the maintaining step is for about 10 minute to about 180 minutes, more preferably, for about 90 minutes.

Preferably, cooling rate after the heating is at about 10 deg/min. Preferably, the obtained precipitate is further maintained at a temperature of about −5° C. to about +5° C., more preferably, at about 0° C. Preferably, the maintaining step is for about 5 minutes to about 180 minutes, more preferably, for about 20 minutes.

The precipitate is further isolated. The isolation may be done by filtration.

Figure 15:
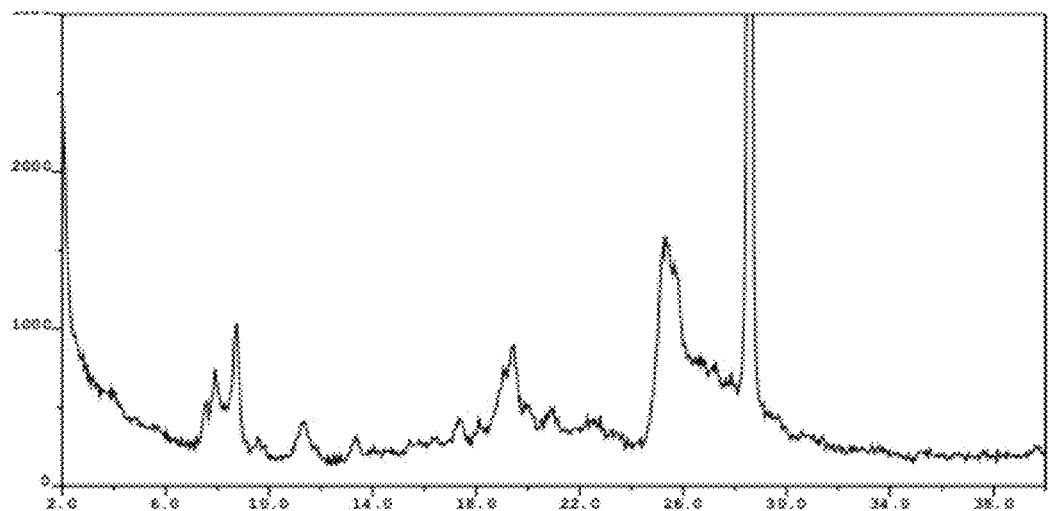
FIG. 15 illustrates a characteristic x-ray powder diffractogram of nilotinib HCl Form T14.

The invention encompasses crystalline Nilotinib HCl, defined herein as Form T14, characterized by data selected from the group consisting of: an x-ray powder diffraction pattern having peaks at about 7.5, 7.9, 8.7, 19.4 and 25.3 degrees two theta±0.2 degrees two theta; an x-ray powder diffraction pattern substantially as depicted in FIG. 15; and combinations thereof. Nilotinib HCl Form T14 may be further characterized by x-ray powder diffraction pattern having additional peaks at about 11.3, 13.4 and 17.4 degrees two theta±0.2 degrees two theta.

Figure 16:
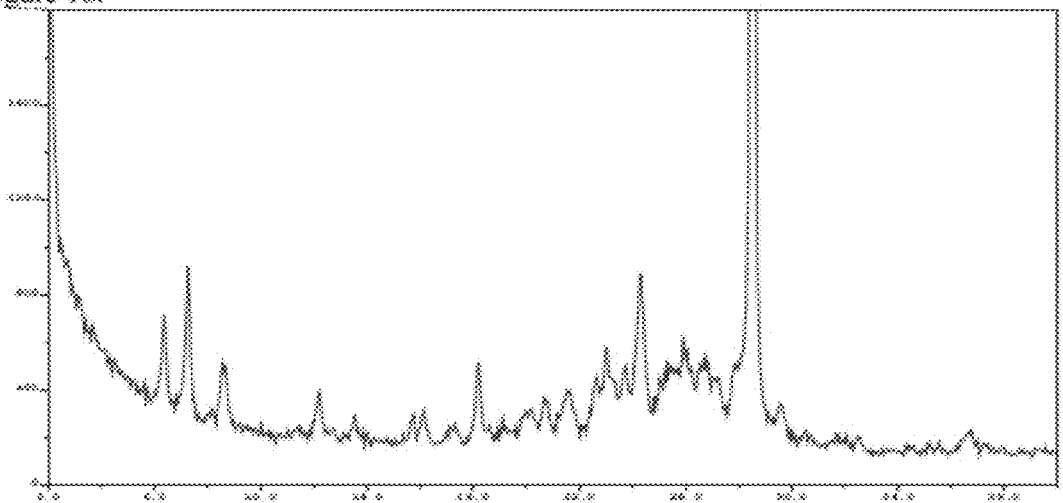
FIG. 16 illustrates a characteristic x-ray powder diffractogram of nilotinib HCl Form T15.

The invention encompasses crystalline Nilotinib HCl, defined herein as Form T15, characterized by data selected from the group consisting of: an x-ray powder diffraction pattern having peaks at about 6.3, 7.3, 8.6, 12.2 and 18.2 degrees two theta±0.2 degrees two theta; an x-ray powder diffraction pattern substantially as depicted in FIG. 16; and combinations thereof. Nilotinib HCl Form T15 may be further characterized by x-ray powder diffraction pattern having additional peaks at about 23.0 and 24.3 degrees two theta±0.2 degrees two theta.

Figure 17:
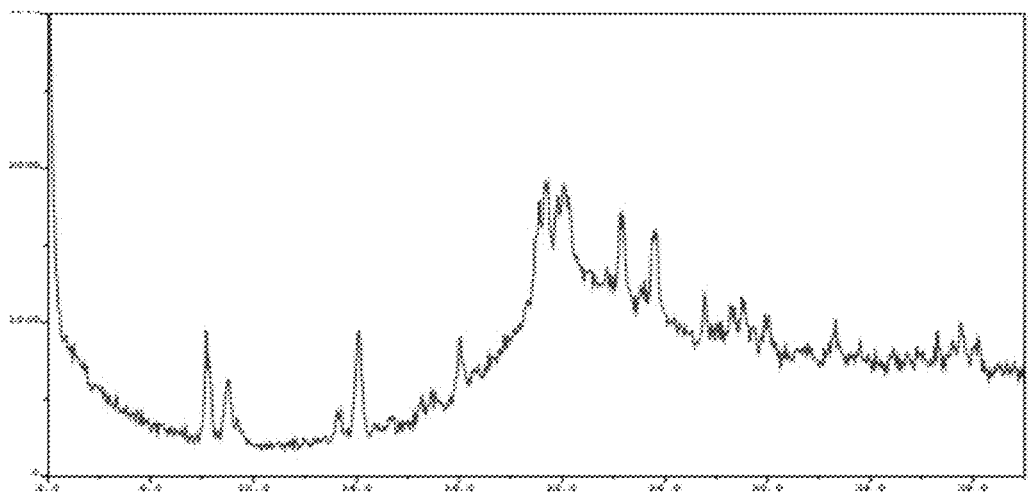
FIG. 17 illustrates a characteristic x-ray powder diffractogram of nilotinib HCl Form T16.

The present invention encompasses crystalline Nilotinib HCl, defined herein as Form T16, characterized by data selected from the group consisting of: an x-ray powder diffraction pattern having peaks at about 8.1, 9.0, 14.1, 18.0 and 21.4 degrees two theta±0.2 degrees two theta; an x-ray powder diffraction pattern substantially as depicted in FIG. 17; and combinations thereof. Nilotinib HCl Form T16 may be further characterized by x-ray powder diffraction pattern having additional peaks at about 21.1, 21.8 and 22.1 degrees two theta±0.2 degrees two theta.

Figure 18:
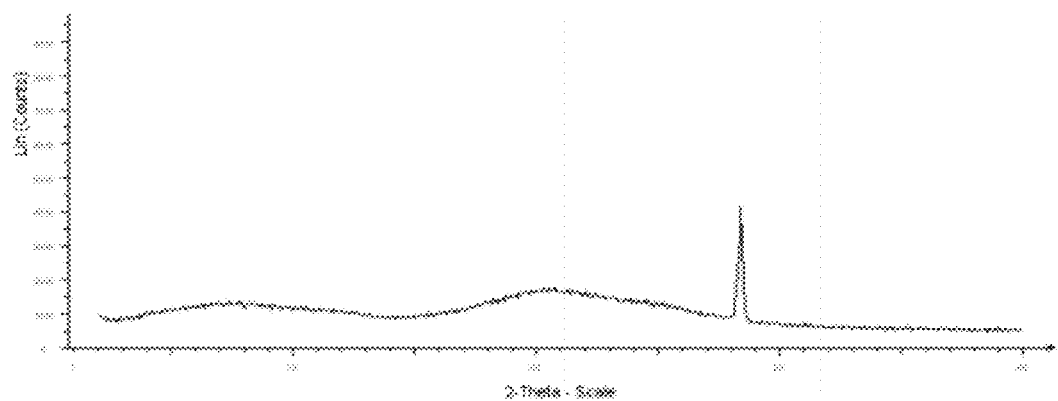
FIG. 18 illustrates a characteristic x-ray powder diffractogram of a solid dispersion of Nilotinib HCl in a combination with hydropropyl cellulose.

The present invention encompasses a solid dispersion of Nilotinib HCl in a combination with a pharmaceutically suitable excipient, characterized by an x-ray powder diffractogram substantially as depicted in FIG. 18.

Pharmaceutically suitable excipients may be polymer or carbohydrates. Non-limiting examples of suitable polymers that can be used as excipients include, either alone or in combination, polyvinylpyrrolidone (PVP or povidone), hydroxypropyl cellulose (HPC), ethyl cellulose hydroxypropylmethylcellulose (HPMC), and HPMC phthalate. Examples of carbohydrates used as crystallization inhibitors include, either alone or in combination, lactose, trehalose, mannitol, sorbitol, ethylcellulose, hydroxyethylcellulose, sodium carboxymethylcellulose (carmellose sodium), calcium carboxymethylcellulose, dextran, acacia, starches, β-cyclodextrin, block copolymers of ethylene oxide and propylene oxide, polyvinyl alcohol, and polyethylene glycol (PEG). Preferably, the excipient is a polymer selected from the group consisting of: hydropropyl cellulose, hydroxylpropyl methyl cellulose and ethyl cellulose.

The present invention also encompasses a process for preparing a solid dispersion of Nilotinib HCl in a combination with pharmaceutically suitable excipient comprising dissolving Nilotinib HCl and a suitable excipient in $C_1$-$C_4$ alcohol; and removing the solvent to obtain the solid dispersion of Nilotinib HCl in a combination with a pharmaceutically suitable excipient.

Preferably, the $C_1$-$C_4$ alcohol is methanol.

The present invention encompasses a process for preparing a solid dispersion of Nilotinib HCl in a combination with pharmaceutically suitable excipient comprising the step of spray drying a solution comprising Nilotinib HCl and a pharmaceutically suitable excipient in $C_1$-$C_4$ alcohol, using an outlet temperature of about 35° C. to about 40° C. Preferably, the inlet temperature is about 60° C. to about 80° C.

Preferably, the process comprises combining Nilotinib HCl with suitable excipient and a $C_1$-$C_4$ alcohol; heating to obtain a solution; and spray drying.

Preferably, the $C_1$-$C_4$ alcohol is methanol.

Preferably, the heating is to a temperature of about 60° C. to about 80° C., more preferably, to a temperature of about 70° C.

Preferably, the spray drying is done at about the same temperature of the heating step.

Figure 19:
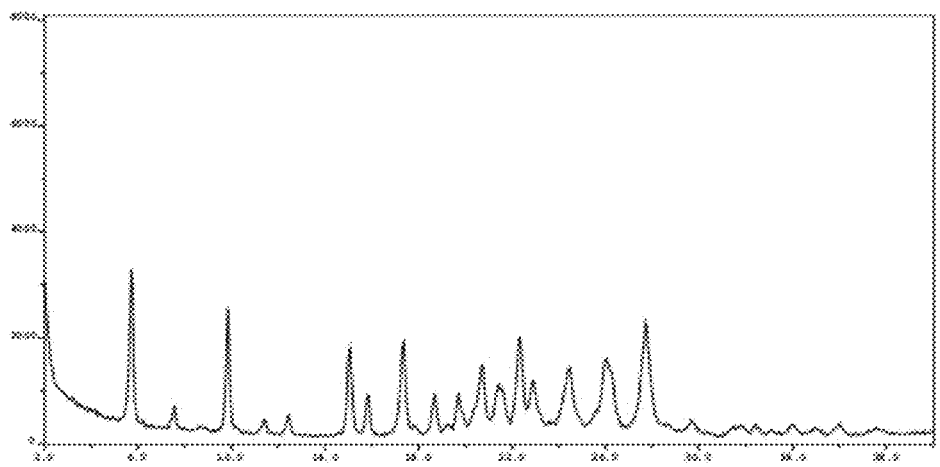
FIG. 19 illustrates a characteristic x-ray powder diffractogram of nilotinib HCl Form T17.
Figure 20:
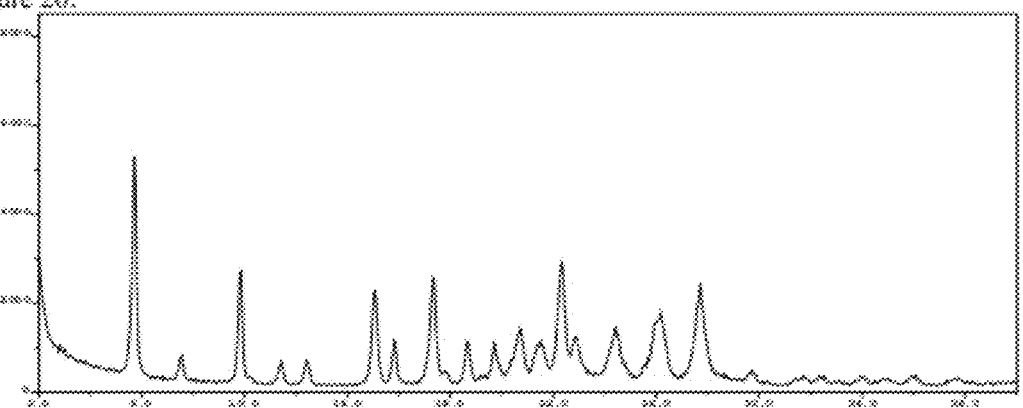
FIG. 20 illustrates a characteristic x-ray powder diffractogram of nilotinib HCl Form T17.
Figure 21:
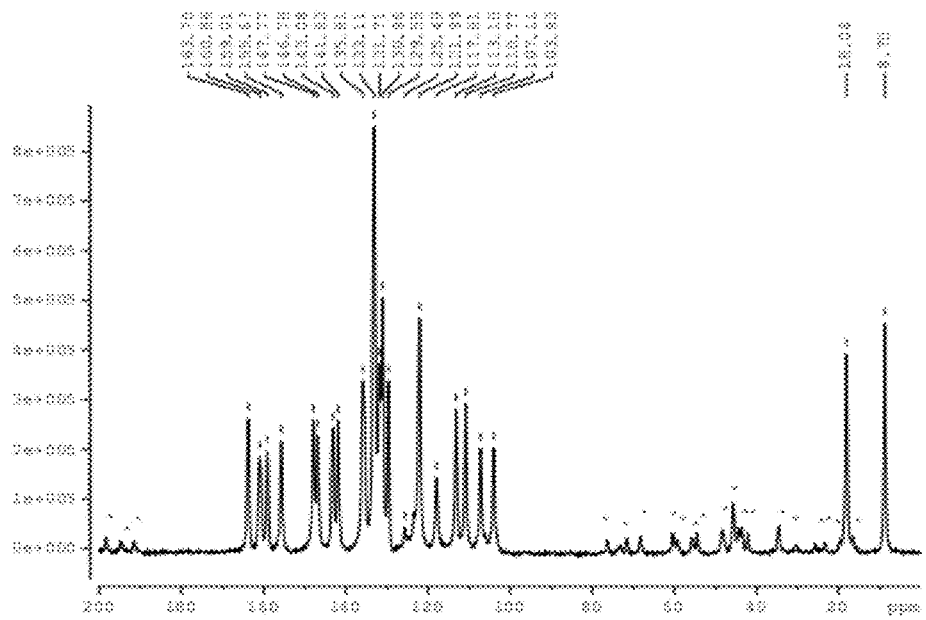
FIG. 21 illustrates a solid-state $^{13}$C NMR spectrum of Nilotinib HCl form T17 in the 0-200 ppm range.
Figure 22:
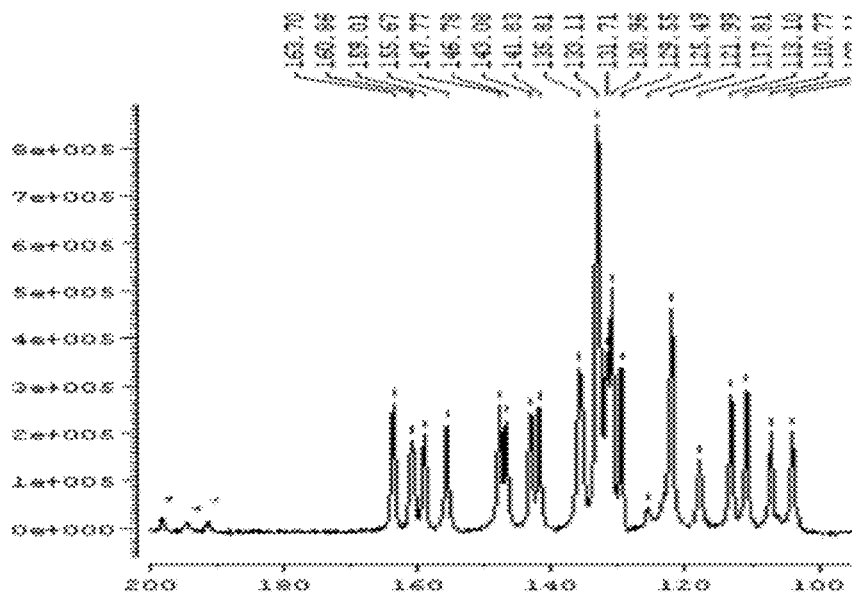
FIG. 22 illustrates a solid-state $^{13}$C NMR spectrum of Nilotinib HCl form T17 in the 100-200 ppm range.

The present invention encompasses crystalline Nilotinib HCl, defined herein as Form T17, characterized by data selected from the group consisting of: an x-ray powder diffraction pattern having peaks at about 5.7, 9.8, 15.0, 15.8 and 17.3 degrees two theta±0.2 degrees two theta; an x-ray powder diffraction pattern substantially as depicted in FIG. 19; an x-ray powder diffraction pattern substantially as depicted in FIG. 20; a solid-state $^{13}C$ NMR spectrum with signals at about and 113.1, 133.1, 160.9±0.2 ppm; a solid-state $^{13}C$ NMR spectrum having chemical shifts differences between the signal exhibiting the lowest chemical shift and another in the chemical shift range of 100 to 180 ppm of about 9.2, 29.2 and 57.0±0.1 ppm, wherein the signal exhibiting the lowest chemical shift in the chemical shift area of 100 to 180 ppm is typically at about 103.9±1 ppm; $^{13}C$ NMR spectrum as depicted in FIG. 21; $^{13}C$ NMR spectrum as depicted in FIG. 22; and combinations thereof. Nilotinib HCl Form T17 may be further characterized by x-ray powder diffraction pattern having additional peaks at about 7.5, 11.4, 18.6, 19.6 and 20.7 degrees two theta±0.2 degrees two theta or at about 7.6, 11.4, 18.7, 19.7 and 20.7 degrees two theta±0.2 degrees two theta.

Typically, Nilotinib HCl crystalline form T17 is anhydrous and does not convert to other forms when heated, while other polymorphs, know in the art, such as Nilotinib HCl form A and Nilotinib HCl form B are converted to other polymorphs as described in WO '870.

The invention also encompasses a process for preparing Nilotinib HCl Form T17 comprising:
 a) combining Nilotinib base form A with ethanol absolute and HCl to obtain a slurry;
 b) heating;
 c) cooling; and
 d) drying.

Preferably, the HCl is dissolved in absolute ethanol or in water. Preferably, when HCl is dissolved in absolute ethanol, the concentration of the HCl in the solution is about 14%, about 13.3% to about 14.1%, about 13.26% to about 14.13%, or about 13.77%. Preferably, when HCl is dissolved in water, the concentration of the HCl in the solution is about 32%.

Preferably, the heating is to a temperature of about 75° C. to about 85° C., more preferably, to about reflux temperature. Preferably, the heating is done while stirring. Preferably, the stirring is done for about 0.5 hour to about 4 hours, more preferably, for about 0.5 hour to about 1.5 hours.

Preferably, following the heating of step b and prior to the cooling of step c, a filtering step is performed. Preferably, the filtering is done under reduced pressure, such as about 20 mbar to about 30 mbar.

Optionally, after the filtering another portion of absolute ethanol is added to the filtrate to form a reaction mixture. The reaction mixture is preferably heated. The heating may be done while stirring. Preferably, the stirring is done for about 10 minutes to about 60 minutes, more preferably, for about 30 minutes. The heating is typically done to a temperature of about 77° C. to about 79° C. Preferably, the heating is done to about reflux temperature.

Preferably, the reaction mixture is seeded while heating. The seeding is preferably done with Nilotinib HCl form T17. Typically, the seeding is done at a temperature of about 72° C. to about 78° C. Preferably, the seeding is done at a temperature of about 76.0° C. to about 76.6° C. Preferably, after the seeding step, a second reaction mixture is obtained. The second reaction mixture is preferably further maintained at a temperature of about 77° C. to about 79° C., more preferably, at about reflux temperature. Preferably, the maintaining step is done for about 15 minutes to about 75 minutes, more preferably, for about 30 minutes to about 60 minutes.

Preferably, the cooling of step c is done to a temperature of about 10° C. to about 0° C., more preferably, to about 6° C. to about 5° C. Preferably, the cooling is done gradually, more preferably, the cooling is done during a period of about 3 hours to about 2 hours. Optionally, while cooling or following the cooling step, absolute ethanol is added.

Optionally, prior to the cooling of step c, an additional cooling step followed by a heating step is done. Preferably, the cooling is to about 60° C. to about 50° C., more preferably, to about 55° C. Typically, the cooling is done gradually. Preferably, the cooling is done for about 2 hours to about 3 hours. Preferably, the heating is done to a temperature of about 77° C. to about 79° C. more preferably, to about reflux temperature After the cooling of step c, a slurry is obtained. Typically, the slurry is stirred. Preferably, the stirring is done at about 0° C. to about 10° C., more preferably, at about 5° C. Preferably, the stirring is done for about 15 minutes to about over night.

Typically, prior to the drying of step d, a filtering step is performed followed by a washing step.

Preferably, the washing is done with absolute ethanol.

Preferably, the drying is done for about over night. Preferably, the drying is done at a temperature of about 60° C. to about 80° C., more preferably, at a temperature of about 70° C. Preferably, the drying is done in a vacuum oven.

Preferably, the process for preparing Nilotinib HCl Form T17 comprises: combining Nilotinib base form A with absolute ethanol and HCl to obtain a slurry; heating; filtering; heating while seeding with crystalline form T17; cooling; adding ethanol absolute; and drying.

The present invention comprises another process for preparing Nilotinib HCl form T17 comprising: slurrying Nilotinib HCl amorphous form with dry acetone or dry tetrafydrofuran (THF) to obtain a slurry; agitating the slurry; and drying to obtain Nilotinib HCl form T17.

Preferably, the acetone or THF are dried over 4 A molecular sieves.

Preferably, the agitating is done by shaking. Preferably, the agitating is done for about 72 hours. Preferably, while agitating the slurry, the temperature is cycled between about 15° C. to about 45° C., more preferably, between about ambient temperature to about 40° C. Typically, each cycle is done for about 4 hours.

Preferably, prior to the drying step the solvent is removed. Preferably, the removing is done by decanting off the solvent, typically, by using a syringe.

Preferably, the drying is done under a nitrogen atmosphere. Preferably, the drying is done overnight.

The present invention further comprises a process for preparing a mixture of Nilotinib HCl form T17 and nilotinib HCl form A comprising: combining Nilotinib HCl amorphous form with dry isopropyl acetate or dry ethyl acetate to obtain a slurry; agitating the slurry; and drying to obtain a mixture of Nilotinib HCl form T17 and Nilotinib HCl form A.

Preferably, the isopropyl acetate or ethyl acetate are dried over 4 A molecular sieves.

Preferably, the agitating is done by shaking. Preferably, the agitating is done for about 72 hours. Preferably, while agitating the slurry, the temperature is cycled between about 15° C. to about 45° C., more preferably, between about ambient temperature to about 40° C. Typically, each cycle is done for about 4 hours.

Preferably, prior to the drying step the solvent is removed. Preferably, the removing is done by decanting off the solvent, typically, by using a syringe.

Preferably, the drying is done under a nitrogen atmosphere. Preferably, the drying is done overnight.

The present invention provides additional process for preparing Nilotinib HCl form T17 comprising: slurrying a mixture of Nilotinib HCl form A and Nilotinib HCl for T17 with IPA or acetonitrile to obtain Nilotinib HCl form T17.

Preferably, the slurrying is done at a temperature of about 0° C. to about 60° C., more preferably, at about 20° C. to about 60° C., most preferably, at about 40° C. Preferably, the slurrying is done for about 1 day to about 5 days, more preferably, for about 3 days.

Typically, the obtained Nilotinib form T17 is further isolated. Preferably, the isolation is done by filtration.

Figure 23:
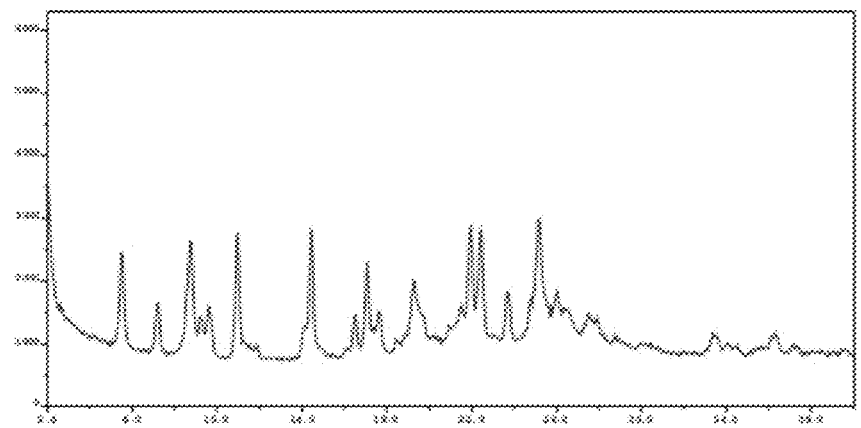
FIG. 23 illustrates a characteristic x-ray powder diffractogram of nilotinib HCl Form T18.

The present invention encompasses crystalline Nilotinib HCl, defined herein as Form T18, characterized by data selected from the group consisting of: an x-ray powder diffraction pattern having peaks at about 5.5, 7.1, 8.7, 9.6 and 10.9 degrees two theta±0.2 degrees two theta; an x-ray powder diffraction pattern having peaks at about 5.5, 7.2, 8.7, 9.6 and 10.9 degrees two theta±0.2 degrees two theta an x-ray powder diffraction pattern substantially as depicted in FIG. 23; and combinations thereof. Nilotinib HCl Form T18 may be further characterized by x-ray powder diffraction pattern having additional peaks at about 14.4, 17.0, 19.2, 21.9 and 22.3 degrees two theta±0.2 degrees two theta or at about 14.4, 17.0, 19.2, 21.9 and 22.4 degrees two theta±0.2 degrees two theta.

Preferably, Nilotinib HCl form T18 is characterized by a combination of x-ray powder diffraction pattern having peaks at about 5.5, 7.1, 8.7, 9.6 and 10.9 degrees two theta±0.2 degrees two theta and an x-ray powder diffraction pattern substantially as depicted in FIG. 23.

The invention also encompasses a process for preparing Nilotinib HCl Form T18 comprising:
  a) combining Nilotinib base form A with absolute ethanol and HCl to obtain a slurry;
  b) heating; and
  c) cooling to obtain Nilotinib HCl form T18.

Preferably, the HCl is dissolved in absolute ethanol or in water. Preferably, when HCl is dissolved in absolute ethanol, the concentration of the HCl in the solution is about 14%, about 13.3% to about 14.1%, about 13.26% to about 14.13%, or about 13.77%. Preferably, when HCl is dissolved in water, the concentration of the HCl in the solution is about 32%.

Preferably, the heating of step b is to a temperature of about 75° C. to about 85° C., more preferably, to about reflux temperature. Preferably, the heating is done while stirring. Preferably, the stirring is done for about 0.5 hour to about 4 hours, more preferably, for about 0.5 hour to about 1.5 hours.

Preferably, following the heating of step b and prior to the cooling of step c, a filtering step is performed. Preferably, the filtering is done under reduced pressure, more preferably, at about 20 mbar to about 30 mbar.

Preferably, after the filtering step and prior to the cooling of step c, a heating step is performed. Typically, the heating is done to a temperature of about 77° C. to about 79° C. Preferably, the heating is done to about reflux temperature.

Preferably, a seeding step is performed while heating. The seeding is preferably done with Nilotinib HCl form T17. Typically, the seeding is done at a temperature of about 72° C. to about 78° C. Preferably, the seeding is done at a temperature of about 76.0° C. to about 76.6° C. Preferably, after the seeding step, a reaction mixture is obtained. The reaction mixture is preferably further maintained at a temperature of about 77° C. to about 79° C., more preferably, the maintaining is at about reflux temperature Preferably, the maintaining step is done for about 15 minutes to about 75 minutes, more preferably, for about 30 minutes to about 60 minutes.

Preferably, the cooling of step c, is to a temperature of about 10° C. to about 0° C., more preferably, at about 6° C. to about 5° C. Preferably, the cooling is done during a period of about 2 hours to about 3 hours, more preferably, for about 2 hours. Optionally, while cooling or following the cooling step, absolute ethanol is added.

After the cooling of step c, a slurry is obtained. Typically, the slurry is stirred. Preferably, the stirring is done at about 0° C. to about 10° C., more preferably, at about 5° C. Preferably, the stirring is done for about 15 minutes to about 45 minutes, more preferably, for about 30 minutes.

The process may further comprise filtering and/or washing steps.

Preferably, the washing is done with absolute ethanol.

Preferably, the process for preparing Nilotinib HCl Form T18 comprises: combining Nilotinib base form A with absolute ethanol and HCl to obtain a slurry; heating; filtering; heating while seeding with crystalline form T17; cooling; adding absolute ethanol; filtering; and washing to obtain Nilotinib HCl form T18.

The present invention provides a process for preparing Nilotinib HCl Form T17 by drying Nilotinib HCl Form T18. The parameters of this process are as described above.

The present invention provides another process for preparing Nilotinib HCl Form T18 comprising: slurrying a mixture of Nilotinib HCl form A and Nilotinib HCl form T17 in absolute ethanol at a temperature of about 55° C. to about 78° C.

Preferably, the slurrying is done at a temperature of about 60° C. to about 75° C. Preferably, the slurrying is done for about 4 hours to about 7 days, more preferably, for about 3 days.

The obtained Nilotinib HCl form T18 is further isolated. Preferably, the isolation is by filtration.

The present invention provides additional process for preparing Nilotinib HCl form T18 comprising: combining Nilotinib HCl form T17 with absolute ethanol; heating; and cooling to obtain Nilotinib HCl form T18.

Optionally, the absolute ethanol has water content of less than about 0.01% w.

Preferably, the heating is to a temperature of about 76° C. to about 78° C., more preferably to about reflux temperature. Preferably, the heating is done while stirring.

Following the heating step and prior to the cooling a reaction mixture is obtained. Preferably, the reaction mixture is maintained at a temperature of about 76° C. to about 78° C., more preferably, at about reflux temperature. Preferably, the maintaining step is done for about 10 minutes to about 30 minutes.

Preferably, the cooling is done to a temperature of about 3° C. to about 7° C., more preferably, to about 5° C. Preferably, the cooling is done during a period of about 2 hours to about 3 hours, more preferably, during about 3 hours.

After the cooling a slurry is obtained. Typically, the slurry is stirred. Preferably, the stirring is done at about 3° C. to about 7° C., more preferably, at about 5° C. Preferably, the stirring is done for about 11 hours to about 17 hours, more preferably, for about 12 hours.

The process may further comprise filtering and/or washing steps. Optionally, the filtering is done under nitrogen environment. Preferably, the washing is done with absolute ethanol.

Figure 24:
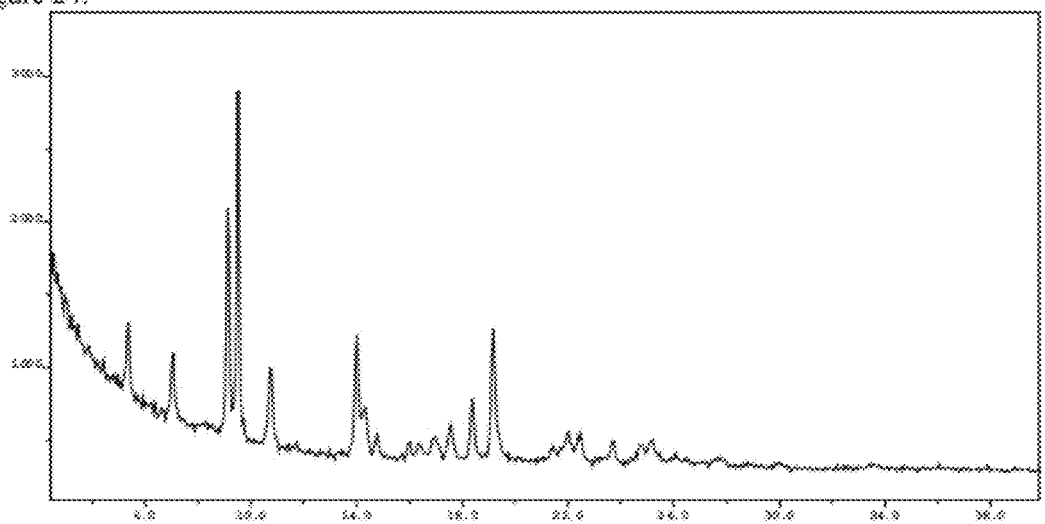
FIG. 24 illustrates a characteristic x-ray powder diffractogram of nilotinib HCl Form T19.

The present invention further encompasses crystalline Nilotinib HCl, defined herein as Form T19, characterized by data selected from the group consisting of: an x-ray powder diffraction pattern having peaks at about 5.5, 7.2, 9.2, 9.6 and 10.9 degrees two theta±0.2 degrees two theta; an x-ray powder diffraction pattern substantially as depicted in FIG. 24; and a combination thereof. Nilotinib HCl Form T19 may be further characterized by x-ray powder diffraction pattern having additional peaks at about 14.1, 14.9, 17.7, 18.5 and 19.3 degrees two theta±0.2 degrees two theta.

Preferably, Nilotinib HCl form T19 is characterized by a combination of x-ray powder diffraction pattern having peaks at about 5.5, 7.2, 9.2, 9.6 and 10.9 degrees two theta±0.2 degrees two theta and an x-ray powder diffraction pattern substantially as depicted in FIG. 24.

The present invention provides a process for preparing Nilotinib HCl Form T19 comprising: slurrying Nilotinib HCl form B in absolute ethanol; heating to a temperature of about 55° C. to about 78° C.; and cooling.

Preferably, the ratio of Nilotinib HCl form B to the absolute ethanol is 35 mg/ml.

Preferably, the slurrying is done at about 20° C. to about 30° C., more preferably, at about 20° C. Preferably, the slurrying is done for about 2 hours to about 15 hours, more preferably, for about 11 hours.

Preferably, the heating is done to a temperature of about 75° C. Preferably, the heating is done at a rate of about 0.1 deg/min to about 10 deg/min, more preferably, at about 2 deg/min Typically, the heating is done while maintaining the slurry. The maintaining step is done at about 75° C. Preferably, the maintaining step is done for about 30 minutes to about 180 minutes, more preferably, for about 90 minutes.

Preferably, the cooling is to a temperature of about 0° C. Preferably, the cooling is done at a rate of about 10 deg/min.

Typically, the cooling is done while maintaining the slurry. The maintaining step is done at a temperature of about 0° C. Preferably, the maintaining step is done for about 1 hour to about 5 hours, more preferably, for about 1 hour.

The obtained Nilotinib HCl form T19 is further isolated. Preferably, the isolation is by filtration.

Nilotinib base form A as used in any of the above described processes may be prepared according to U.S. Pat. No. 7,169,791, which is incorporated herein by reference.

Nilotinib HCl form A as used in any of the above described processes may be prepared according to WO '870, which is incorporated herein by reference.

Nilotinib HCl form B as used in any of the above described processes may be prepared according to WO '871, which is incorporated herein by reference.

Nilotinib HCl amorphous form as used in any of the above described processes may be prepared according to WO '870, which is incorporated herein by reference.

Pharmaceutical compositions comprising one or more compounds of the present invention, may be formulated, as is well known in the prior art, such as by reference to known compilations as *Remington's Pharmaceutical Sciences*, Mack Publishing Co., Easton, Pa., USA, which is incorporated herein by reference.

The present invention further encompasses a pharmaceutical composition comprising any one, or combination, of crystalline Forms T1-T19 and/or a solid dispersion of Nilotinib HCl in a combination with pharmaceutically suitable excipient, described above and at least one pharmaceutically acceptable excipient.

Having thus described the invention with reference to particular preferred embodiments and illustrative examples, those in the art can appreciate modifications to the invention as described and illustrated that do not depart from the spirit and scope of the invention as disclosed in the specification. The Examples are set forth to aid in understanding the invention but are not intended to, and should not be construed to limit its scope in any way.

EXAMPLES

Spray Drying

Spray drying was performed using a Buchi Mini spray dryer B-191 using a standard nozzle 1.5 mm in diameter with a nozzle cap of 1.5 mm. Pump dosage: 10%; aspirator rate: 100%; air spray flow: 600-650 Liter/Hr.

X-Ray Powder Diffraction:

The X-ray powder diffraction of Nilotinib HCl forms T1-T19 was performed on an ARL X-ray powder diffractometer model X'TRA-019 and model X'TRA-030, with a Peltier detector. Copper $K\alpha_1$ radiation ($\lambda$=1.5418 Å) was used. The sample holder was a round standard aluminum sample holder with round zero background plate (quartz or silicon). The scanning parameters were: range: 2-40 degrees two-theta; scan mode: continuous scan; step size: 0.05°; and scan rate: 3 degrees/minute.

The X-ray powder diffraction of the solid dispersion of Nilotinib HCl in a combination with cellulose was performed by Bruker X-Ray powder diffractometer model D8 advance equipped with lynxEye. Copper $K\alpha_1$ radiation ($\lambda$=1.5418 Å) was used. The scanning parameters were: range: 2-40 degrees two-theta; step size: 0.05°; time per step: 0.5 sec; and divergence slit: 1 degree.

The peak positions were determined by using silicon powder as internal standard in an admixture with the sample measured. The position of the silicon (111) peak was corrected to be 28.45 degrees two theta. The positions of the peaks were corrected respectively (no corrections were performed on the presented diffractograms in the figures).

$^{13}$C-NMR $^{13}$C-NMR spectra were obtained on Bruker Avance II+500.

The instrument parameters: SB probe using 4 mm rotors; Magic angle was set using KBr; Homogeneity of magnetic field checked using adamantine; Parameters for Cross polarization optimized using glycine; Spectral reference set according to glycine as external standard (176.03 ppm for low field carboxyl signal).

The Scanning parameters: Magic Angle Spinning Rate: 11 kHz; Pulse Program: cp with tppm15 during decoupling; Delay time: 2 s; Number of Scans: 2048

Example 1

Preparation of Nilotinib HCl Form T1

To a 1 ml vial were added 50 mg of Nilotinib HCl (form B) and DMSO (400 μl). The slurry was stirred at 700 rpm at room temperature (20-30° C.) for 24 hours. After 24 hours stirring, the solid was filtered under reduced pressure and was analyzed by XRD.

Example 2

Preparation of Nilotinib HCl Form T2

Nilotinib base form A (0.5 g, 0.94 mmol) was suspended in ethanol absolute (4 ml), then an HCl solution (0.23 mL, 19.48% in IPA) was added and the reaction mixture became yellow. The slurry was stirred at room temperature (20-30° C.) for 16 h. The product was filtered and washed twice with ethanol absolute (1.5 ml). The solid was dried under vacuum oven at 50° C. overnight to yield Nilotinib HCl form T2.

Example 3

Preparation of Nilotinib HCl Form T2

Nilotinib base form A (0.5 g, 0.94 mmol) was suspended in iso-propanol (4 ml), then HCl solution (0.23 mL, 19.48% in IPA) was added and the reaction mixture became yellow. The slurry was stirred at room temperature (20-30° C.) for 16 h. The product was filtered and washed twice with. iso-propanol (1.5 ml). The solid was dried under vacuum oven at 50° C. overnight to yield Nilotinib HCl form T2.

Example 4

Preparation of Nilotinib HCl Form T3

Nilotinib base form A (0.5 g, 0.94 mmol) was suspended in ethanol 95% (4 ml), then HCl solution (0.23 mL, 19.48% in IPA) was added and the reaction mixture became yellow. The slurry was stirred at room temperature (20-30° C.) for 16 h. The product was filtered and washed twice with ethanol 95% (1.5 ml). The solid was dried under vacuum oven at 50° C. overnight to yield the Nilotinib HCl form T3.

Example 5

Preparation of Nilotinib HCl Form T4

Nilotinib base form A (0.5 g, 0.94 mmol) was suspended in 1-propanol (4 ml), then HCl solution (0.23 mL, 19.48% in IPA) was added and the reaction mixture became yellow. The slurry was stirred at room temperature (20-30° C.) for 16 h. The product was filtered and washed twice with 1-propanol (1.5 ml). The solid was dried under vacuum oven at 50° C. overnight to yield Nilotinib HCl form T4.

Example 6

Preparation of Nilotinib HCl Form T5

Nilotinib base form A (0.5 g, 0.94 mmol) was suspended in n-butanol (4 ml), then HCl solution (0.23 mL, 19.48% in IPA) was added and the reaction mixture became yellow. The slurry was stirred at room temperature (20-30° C.) for 16 h. The product was filtered and washed twice with n-butanol (1.5 ml). The solid was dried under vacuum oven at 50° C. overnight to yield Nilotinib HCl form T5.

Example 7

Preparation of Nilotinib HCl Form T6

Nilotinib base form A (0.5 g, 0.94 mmol) was suspended in 2-butanol (4 ml), then HCl solution (0.23 mL, 19.48% in IPA) was added and the reaction mixture became yellow. The slurry was stirred at room temperature (20-30° C.) for 16 h. The product was filtered and washed twice with of 2-butanol (1.5 ml). The solid was dried under vacuum oven at 50° C. overnight to yield Nilotinib HCl form T6.

Example 8

Preparation of Nilotinib HCl Form T6

Nilotinib base form A (0.5 g, 0.94 mmol) was suspended in tert-butanol (4 ml), then HCl solution (0.23 mL, 19.48% in IPA) was added and the reaction mixture became yellow. The slurry was stirred at room temperature (20-30° C.) for 16 h. The product was filtered and washed twice with tert-butanol (1.5 ml). The solid was dried under vacuum oven at 50° C. overnight to yield Nilotinib HCl form T6.

Example 9

Preparation of Nilotinib HCl Form T6

Nilotinib base form A (0.5 g, 0.94 mmol) was suspended in 2-pentanol (4 ml), then HCl solution (0.23 mL, 19.48% in IPA) was added and the reaction mixture became yellow. The slurry was stirred at room temperature (20-30° C.) for 16 h. The product was filtered and washed twice with 2-pentanol (1.5 ml). The solid was dried under vacuum oven at 50° C. overnight to yield Nilotinib HCl form T6.

Example 10

Preparation of Nilotinib HCl Form T7

To 50 ml flask vessel were added Nilotinib HCl form B (0.5 g, 0.78 mmol) and benzyl alcohol (4 ml). The slurry was stirred for 24 hours at ambient temperature (20-30° C.), filtered and dried under vacuum oven at 50° C. overnight to yield Nilotinib HCl form T7.

Example 11

Preparation of Nilotinib HCl Form T8

To 50 ml flask vessel were added Nilotinib HCl form B (0.5 g, 0.78 mmol) and DMA (4 ml). The slurry was stirred for 24 hours at ambient temperature (20-30° C.), filtered and dried under vacuum oven at 50° C. overnight to yield Nilotinib HCl form T8.

Example 12

Preparation of Nilotinib HCl Form T9

To 50 ml flask vessel were added Nilotinib HCl form B (0.5 g, 0.78 mmol) and chlorobenzene (8 vol). The slurry was stirred for 24 hours at ambient temperature (20-30° C.), filtered and dried under vacuum oven at 50° C. overnight to yield Nilotinib HCl form T9.

Example 13

Preparation of Nilotinib HCl Form T10

To 50 ml flask vessel were added Nilotinib HCl form B (0.5 g, 0.78 mmol) and ethylene glycol (4 ml). The slurry was stirred for 24 hours at ambient temperature (20-30° C.), filtered and dried under vacuum oven at 50° C. overnight to yield Nilotinib HCl form T10.

Example 14

Preparation of Nilotinib HCl Form T11

Nilotinib HCl form B (35 mg) in 1-propanol (1 mL) was cooled to 0° C., heated up to 65° C. with 0.1 deg/min, cooled back to 0° C. with 0.1 deg/min, slurried at 0° C. for 3 days and filtered to yield Nilotinib HCl form T11.

Example 15

Preparation of Nilotinib HCl Form T12

Nilotinib HCl form B (50 mg) in Butyl lactate (1 mL) was cooled to 0° C., heated to 78° C. with 0.1 deg/min heating rate, cooled to 0° C. with 0.1 deg/min heating rate, slurried at 0° C. for during 2 days and filtered to yield Nilotinib HCl form T12.

Example 16

Preparation of Nilotinib HCl Form T13

Nilotinib HCl form B (35 mg) in absolute ethanol (1 mL) was cooled to 0° C., heated to 75° C. with 2 deg/min. At 75° C. the Nilotinib HCl Form B was totally dissolved. The Nilotinib HCl absolute ethanol mixture was slurried at 75° C. for 90 minutes, cooled to 0° C. with 10 deg/min. At 0° C. crystallization was observed. The compound was slurried at 0° C. for 20 minutes after the crystallization and filtered to yield Nilotinib HCl form T13.

Example 17

Preparation of Nilotinib HCl Form T14

To a 50 mL round bottom flask were added Nilotinib HCl Form B (1.5 g) and Benzyl alcohol (12 ml). The slurry was stirred for 24 hours at 25° C. The mixture was filtered and dried at 50° C. vacuum oven over night to yield Nilotinib HCl form T14.

Example 18

Preparation of Nilotinib HCl Form T15

To a 50 mL round bottom flask were added Nilotinib HCl Form B (1.5 g) and DMA (12 ml). The slurry was stirred for 24 hours at 25° C. The mixture was filtered and dried at 50° C. vacuum oven over night to yield Nilotinib HCl form T15.

Example 19

Preparation of Nilotinib HCl Form T16

To a 50 mL round bottom flask were added Nilotinib HCl Form B (1.5 g) and ethylene glycol (12 ml). The slurry was stirred for 24 hours at 25° C. The mixture was filtered and dried at 50° C. vacuum oven over night to yield Nilotinib HCl form T16.

Example 20

Preparation of a Solid Dispersion of Nilotinib HCl in a Combination with Hydropropyl Cellulose Nilotinib HCl form B (5 g) and Hydropropyl cellulose (5 g) were slurried in methanol (400 mL) and heated to 60° C. until dissolution. The solution was spray dried in a Buchi Mini spray drier at 60° C. to form a solid dispersion of Nilotinib HCl in a combination with Hydropropyl cellulose Example 21

Preparation of a Solid Dispersion of Nilotinib HCl in a Combination with Hydroxypropyl Methyl Cellulose Nilotinib HCl form B (5 g) and Hydroxypropyl methyl cellulose (5 g) were slurried in methanol (400 mL) and heated to 70° C. until dissolution. The solution was spray dried in a Buchi Mini spray drier at 70° C. to form a solid dispersion of Nilotinib HCl in a combination with Hydroxypropyl methyl cellulose.

Example 22

Preparation of a Solid Dispersion of Nilotinib HCl in a Combination with Ethyl Cellulose Nilotinib HCl form B (5 g) and Ethyl cellulose (5 g) were slurried in methanol (400 mL) and heated to 70° C. until dissolution. The solution was spray dried in a Buchi Mini spray drier at 70° C. to form a solid dispersion of Nilotinib HCl in a combination with Ethyl cellulose.

Example 23

Preparation of Nilotinib HCl Form T17

To 1 Liter reactor was added Nilotinib-base form A (20 g, 0.04 mol), absolute ethanol (188 ml) and 13.77% HCl solution in absolute ethanol (10 g, 0.04 mol). The slurry was heated to reflux, mild dissolution occurred during the stirring, and the mixture was filtered under reduced pressure. During the filtration precipitation occurred. Absolute ethanol was added (120 ml), and the precipitate was returned to the reactor. The mixture was heated to reflux until dissolution and stirred for 30 minutes, then cooled gradually to 5° C. over 3 h. While cooling, absolute ethanol was added (200 ml) and the slurry stirred at 5° C. for 30 minutes, filtered, washed with absolute ethanol, and dried over night at 70° C. in vacuum oven to yield Nilotinib-HCl form T17 (18.4 g, 83% yield).

Example 24

Preparation of Nilotinib HCl Form T17

To a 1 Liter reactor was added Nilotinib-base form A (20 g, 0.04 mol), absolute ethanol (188 ml) and 13.77% HCl solution in absolute ethanol (10 g, 0.04 mol). The slurry was heated to reflux, dissolution occurred during the stirring, and the mixture was filtered under reduced pressure. The Filtrate was fed back to the reactor and heated back to reflux. At 76.6° C. the solution was seeded with 0.2 g of dry material obtained by the process of example 23. Precipitation was observed. Then, it was maintained at reflux for 1 h, followed by cooling for 2 h to 6° C. At 6° C. absolute ethanol was added (300 ml) and the slurry stirred at 5° C. for 30 minutes, filtered, washed with absolute ethanol, and dried over night at 70° C. in vacuum oven to yield Nilotinib-HCl form T17 (18.4 g, 83% yield).

Example 25

Preparation of Nilotinib HCl Form T17

To a 1 Liter reactor was added Nilotinib-base form A (20 g, 0.04 mol), absolute ethanol (200 ml), and HCl 32% solution in water (6.45 g, 0.04 mol). The slurry was heated to reflux, dissolution occurred during the stirring, and the mixture was filtered under reduced pressure. The Filtrate was fed to second reactor and heated back to reflux. At 76.0° C. the solution was seeded with 0.2 g of dry material obtained by the process of example 23. Precipitation was observed. Then, maintained at reflux for 0.5 h, followed by cooling for 2 h to 5° C. During cooling at 20° C. absolute ethanol was added (100 ml) and the slurry stirred till reaching to 5° C., filtered, washed with absolute ethanol, and dried over night at 70° C. in vacuum oven to yield Nilotinib-HCl form T17 (16.3 g, 73% yield).

Example 26

Preparation of Nilotinib HCl Form T17

To 1 Liter reactor was added Nilotinib-base form A (20 g, 0.04 mol), absolute ethanol (188 ml) and 13.77% HCl solution in ethanol abs. (10 g, 0.04 mol). The slurry was heated to reflux, mild dissolution occurred during the stirring, and the mixture was filtered under reduced pressure. During the filtration precipitation occurred. The precipitate was returned to the reactor. The mixture was heated to reflux until dissolution occurred at 65° C. and then cooled gradually to 55° C. During cooling, the solution precipitated at 60° C. The slurry was heated to reflux and cooled for 3 hours to 5° C. The slurry stirred at 5° C. over night, and ethanol abs. was added (100 ml) before filtration. The material filtered, washed with ethanol abs., and dried over night at 70° C. in vacuum oven to yield Nilotinib-HCl form T17 (19 g, 95% yield).

Example 27

Preparation of Nilotinib HCl Form T17

Amorphous Nilotinib hydrochloride (26.1 mg) was weighed into a Japanese vial and acetone (1.25 ml) which had been dried over 4 A molecular sieves, was added to the solid. The vial was sealed and the resulting slurry was shaken using a Heidolph Titramax 1000 platform which was linked to a Heidolph Inkubator 1000 as the temperature was cycled between ambient temperature (20-30° C.) and 40° C. every 4 hours. After a total of 72 hours the sample was removed and the excess solvent was decanted off using a syringe. The residual solid was dried under a flow of nitrogen overnight (~18 hours) to give T17.

Example 28

Preparation of Nilotinib HCl Form T17

Amorphous Nilotinib hydrochloride (25.4 mg) was weighed into a Japanese vial and tetrahydrofuran (1.25 ml), which had been dried over 4 A molecular sieves, was added to the solid. The vial was sealed and the resulting slurry was shaken using a Heidolph Titramax 1000 platform which was linked to a Heidolph Inkubator 1000 as the atmospheric temperature was cycled between ambient temperature (20-30° C.) and 40° C. every 4 hours. After a total of 72 hours the sample was removed and the excess solvent was decanted off using a syringe. The residual solid was dried under a flow of nitrogen overnight (~18 hours) to give T17.

Example 29

Preparation of a Mixture of Nilotinib HCl Form T17 and Nilotinib HCl Form A

Amorphous Nilotinib hydrochloride (26.1 mg) was weighed into a Japanese vial and isopropyl acetate (1.25 ml) which had been dried over 4 A molecular sieves, was added to the solid. The vial was sealed and the resulting slurry was shaken using a Heidolph Titramax 1000 platform which was linked to a Heidolph Inkubator 1000 as the temperature was cycled between ambient temperature (20-30° C.) and 40° C. every 4 hours. After a total of 72 hours the sample was removed and the excess solvent was decanted off using a syringe. The residual solid was dried under a flow of nitrogen overnight (~18 hours) to give mixture of T17 and form A.

Example 30

Preparation of a Mixture of Nilotinib HCl Form T17 and Nilotinib HCl Form A

Amorphous Nilotinib hydrochloride (26.1 mg) was weighed into a Japanese vial and ethyl acetate (1.25 ml) which had been dried over 4 A molecular sieves, was added to the solid. The vial was sealed and the resulting slurry was shaken using a Heidolph Titramax 1000 platform which was linked to a Heidolph Inkubator 1000 as the temperature was cycled between ambient temperature (20-30° C.) and 40° C. every 4 hours. After a total of 72 hours the sample was removed and the excess solvent was decanted off using a syringe. The residual solid was dried under a flow of nitrogen overnight (~18 hours) to give mixture of T17 and form A.

Example 31

Preparation of Nilotinib HCl Form T17

25 mg of Nilotinib HCl Form A and 10 mg Form T17 mixture was slurried at 40 C in 1 ml IPA for 3 days. At the end of the slurry the sample was filtered, analyzed by XRD and found to be mainly Form T17.

Example 32

Preparation of Nilotinib HCl Form T17

25 mg of Nilotinib HCl Form A and 10 mg Form T17 mixture was slurried at 40 C in 1 ml Acetonitrile for 3 days. At the end of the slurry the sample was filtered, analyzed by XRD and found to be mainly Form T17.

Example 33

Preparation of Nilotinib HCl Form T18

To 1 Liter reactor was added Nilotinib-base form A (20 g, 0.04 mol), ethanol absolute (188 ml) and 13.77% HCl solution in ethanol abs. (10 g, 0.04 mol). The slurry was heated to reflux, dissolution occurred during the stirring, and the mixture was filtered under reduced pressure. The Filtrate was fed back to the reactor and heated back to reflux. At 76.6° C. the solution was seeded with 0.2 g of dry material obtained by the process of example 23. Precipitation was observed. Then, the solution was maintained at reflux for 1 h, followed by cooling for 2 h to 6° C. At 6° C. ethanol abs. was added (300 ml) and the slurry stirred at 5° C. for 30 minutes, filtered, washed with ethanol abs. to yield Nilotinib-HCl form T18.

Example 34

Preparation of Nilotinib HCl Form T18

To 1 Liter reactor was added Nilotinib-base form A (20 g, 0.04 mol), ethanol absolute (200 ml), and HCl 32% solution in water (6.45 g, 0.04 mol). The slurry was heated to reflux, dissolution occurred during the stirring, and the mixture was filtered under reduced pressure. The Filtrate was fed to second reactor and heated back to reflux. At 76.0° C. the solution was seeded with 0.2 g of dry material obtained by the process of example 23. Precipitation was observed. Then, the solution was maintained at reflux for 0.5 h, followed by cooling for 2 h to 5° C. During cooling at 20° C. ethanol abs. was added (100 ml) and the slurry stirred till reaching to 5° C., filtered, washed with ethanol abs. to yield Nilotinib-HCl form T18.

Example 35

Preparation of Nilotinib HCl Form T18

50 mg of Nilotinib HCl Form A and Nilotinib HCl Form T17 mixture was slurried at 75° C. in 1 ml abs. ethanol during 3 days. At the end of the slurry the sample was filtered, analyzed by XRD and found to be Form T18.

Example 36

Preparation of Nilotinib HCl Form T18

50 mg of Nilotinib HCl Form A and Nilotinib HCl Form T17 mixture was slurried at 60° C. in 1 ml abs. ethanol during 3 days. At the end of the slurry the sample was filtered, analyzed by XRD and found to be Form T18.

Example 37

Preparation of Nilotinib HCl Form T18

To 1 Liter reactor was added Nilotinib-HCl form T17 (11.2 g, 0.02 mol) and ethanol absolute (224 ml). The slurry was heated to reflux: no dissolution occurred during the stirring. Then, the slurry was maintained at reflux for 0.5 h, followed by cooling for 3 h to 5° C. The slurry was stirred at 5° C. for 12 hr, filtered and washed with ethanol abs. to yield Nilotinib-HCl form T18.

Example 38

Preparation of Nilotinib HCl Form T18

To a 1 ml vial was added Nilotinib-HCl form T17 (50.8 mg, $8.97*10^{-5}$ mol) and ethanol absolute extra dry (1.016 ml). The slurry was heated to reflux: no dissolution occurred during the stirring. Then, the slurry was maintained at reflux for 10 minutes, followed by cooling in 3 h to 5° C. The slurry was stirred at 5° C. for 12 hr, then filtered under $N_2(g)$ environment. to yield Nilotinib-HCl form T18.

Example 39

Preparation of Nilotinib HCl Form T19

35 mg Nilotinib HCl Form B in 1 ml abs. ethanol was slurried during 11 hours at 20° C., and then heated to 75° C. with 2 deg/min. At 75° C. the Nilotinib HCl was not dissolved. The Nilotinib HCl abs. ethanol mixture was slurried at 75° C. during another 90 min, and then it was cooled to 0° C. with 10 deg/min. The compound was slurried at 0° C. during 1 hour. At the end of the slurry the sample was filtered, analyzed by XRD and found to be Form T19.

What is claimed is:
1. A crystalline Nilotinib HCl, characterized by data selected from the group consisting of:
an x-ray powder diffraction pattern having peaks at about 5.7, 9.8, 15.0, 15.8 and 17.3 degrees two theta±0.2 degrees two theta, and also having peaks at about 7.5, 11.4, 18.6, 19.6 and 20.7 degrees two theta±0.2 degrees two theta;
an x-ray powder diffraction pattern substantially as depicted in FIG. 19;
an x-ray powder diffraction pattern substantially as depicted in FIG. 20;
a solid-state $^{13}C$ NMR spectrum with signals at about 113.1, 133.1, and 160.9±0.2 ppm;
a solid-state $^{13}C$ NMR spectrum having chemical shifts differences between the signal exhibiting the lowest chemical shift and another in the chemical shift range of 100 to 180 ppm of about 9.2, 29.2 and 57.0±0.1 ppm, wherein the signal exhibiting the lowest chemical shift in the chemical shift area of 100 to 180 ppm is typically at about 103.9±1 ppm;
a $^{13}C$ NMR spectrum as depicted in FIG. 21;
a $^{13}C$ NMR spectrum as depicted in FIG. 22; and combinations thereof.
2. The crystalline Nilotinib HCl of claim 1, characterized by an x-ray powder diffraction pattern having peaks at about 5.7, 9.8, 15.0, 15.8 and 17.3 degrees two theta±0.2 degrees two theta, and also having peaks at about 7.5, 11.4, 18.6, 19.6 and 20.7 degrees two theta±0.2 degrees two theta.
3. The crystalline Nilotinib HCl of claim 1, characterized by an x-ray powder diffraction pattern substantially as depicted in FIG. 19.
4. The crystalline Nilotinib HCl of claim 1, characterized by an x-ray powder diffraction pattern substantially as depicted in FIG. 20.
5. The crystalline Nilotinib HCl of claim 1, characterized by a solid-state $^{13}C$ NMR spectrum with signals at about 113.1, 133.1, 160.9±0.2 ppm.
6. The crystalline Nilotinib HCl of claim 1, characterized by a solid-state $^{13}C$ NMR spectrum having chemical shifts differences between the signal exhibiting the lowest chemical shift and another in the chemical shift range of 100 to 180 ppm of about 9.2, 29.2 and 57.0±0.1 ppm, wherein the signal exhibiting the lowest chemical shift in the chemical shift area of 100 to 180 ppm is typically at about 103.9±1 ppm.
7. The crystalline Nilotinib HCl of claim 1, characterized by $^{13}C$ NMR spectrum as depicted in FIG. 21.
8. The crystalline Nilotinib HCl of claim 1, characterized by $^{13}C$ NMR spectrum as depicted in FIG. 22.
9. The crystalline Nilotinib HCl of claim 2, further characterized by x-ray powder diffraction pattern having peaks at about 7.6, 11.4, 18.7, 19.7 and 20.7 degrees two theta±0.2 degrees two theta.
10. The crystalline Nilotinib HCl of claim 1, wherein the crystalline form is anhydrous.
11. The crystalline Nilotinib HCl of claim 1, having less than about 10% w/w of Nilotinib HCl form A.
12. A process for preparing Nilotinib HCl of claim 1 comprising: a) combining Nilotinib base form A with absolute ethanol and HCl to obtain a slurry; b) heating; c) cooling; and d) drying to obtain Nilotinib HCl of claim 1.
13. A process for preparing Nilotinib HCl of claim 1 comprising: slurrying Nilotinib HCl amorphous form with dry acetone or dry tetrahydrofuran (THF) to obtain a slurry; agitating the slurry; and drying the slurry to obtain Nilotinib HCl of claim 1.
14. A process for preparing a mixture of Nilotinib HCl of claim 1, and nilotinib HCl form A comprising: slurrying Nilotinib HCl amorphous form with dry isopropyl acetate or dry ethyl acetate to obtain a slurry; agitating the slurry; and drying the slurry to obtain a mixture of Nilotinib HCl of claim 1 and Nilotinib HCl form A.
15. A process for preparing Nilotinib HCl of claim 1, comprising: slurrying a mixture of Nilotinib HCl form A and Nilotinib HCl of claim 1 with IPA or acetonitrile to obtain Nilotinib HCl of claim 1.
16. A crystalline Nilotinib HCl, characterized by data selected from the group consisting of: an x-ray powder diffraction pattern having peaks at about 5.5, 7.1, 8.7, 9.6 and 10.9 degrees two theta±0.2 degrees two theta; an x-ray powder diffraction pattern having peaks at about 5.5, 7.2, 8.7, 9.6 and 10.9 degrees two theta±0.2 degrees two theta; an x-ray powder diffraction pattern substantially as depicted in FIG. 23; and combinations thereof.
17. A process for preparing Nilotinib HCl of claim 16 comprising: a) combining Nilotinib base form A with absolute ethanol and HCl to obtain a slurry; b) heating; and c) cooling to obtain nilotinib HCl.
18. A process for preparing Nilotinib HCl of claim 1 by drying crystalline Nilotinib HCl, characterized by data selected from the group consisting of: an x-ray powder diffraction pattern having peaks at about 5.5, 7.1, 8.7, 9.6 and 10.9 degrees two theta±0.2 degrees two theta; an x-ray powder diffraction pattern having peaks at about 5.5, 7.2, 8.7, 9.6 and 10.9 degrees two theta±0.2 degrees two theta; an x-ray powder diffraction pattern substantially as depicted in FIG. 23; and combinations thereof.

19. A process for preparing Nilotinib HCl of claim 16 comprising: slurrying a mixture of Nilotinib HCl form A and Nilotinib HCl of claim 1 in absolute ethanol at a temperature of about 55° C. to about 78° C.

20. A process for preparing Nilotinib HCl of claim 16 comprising: combining Nilotinib HCl of claim 1 with absolute ethanol; heating; and cooling to obtain Nilotinib HCl.

21. A crystalline Nilotinib HCl, characterized by data selected from the group consisting of: an x-ray powder diffraction pattern having peaks at about 5.5, 7.2, 9.2, 9.6 and 10.9 degrees two theta±0.2 degrees two theta; an x-ray powder diffraction pattern substantially as depicted in FIG. 24; and combinations thereof.

22. A process for preparing Nilotinib HCl of claim 21 comprising: slurrying Nilotinib HCl form B in absolute ethanol at a temperature of about 20° C. to about 30° C.; heating to a temperature of about 55° C. to about 78° C.; and cooling.

23. A crystalline Nilotinib HCl, characterized by data selected from the group consisting of: an x-ray powder diffraction pattern having peaks at about 7.4, 8.9 and 20.8 degrees two theta±0.2 degrees two theta and at least two more peaks selected from the group consisting of 5.6, 10.9, 11.1, 13.8, 14.1, 21.5, 21.8 and 22.4 degrees two theta±0.2 degrees two theta; an x-ray powder diffraction pattern substantially as depicted in FIG. 1; an x-ray powder diffraction pattern having peaks at about 5.6, 7.4, 8.9, 10.9 and 20.8 degrees two theta±0.2 degrees two theta; an x-ray powder diffraction pattern substantially as depicted in FIG. 2; and combinations thereof.

24. A process for preparing nilotinib HCl of claim 23 comprising slurrying Nilotinib HCl form B in dimethyl sulfoxide ("DMSO").

25. A pharmaceutical composition comprising a crystalline form of Nilotinib HCl as defined in claim 1 in combination with at least one pharmaceutically acceptable excipient.

26. A crystalline Nilotinib HCl, characterized by data selected from the group consisting of:
an x-ray powder diffraction pattern having peaks at about 5.7, 9.8, 15.0, 15.8 and 17.3 degrees two theta±0.2 degrees two theta;
an x-ray powder diffraction pattern substantially as depicted in FIG. 19;
an x-ray powder diffraction pattern substantially as depicted in FIG. 20;
a solid-state $^{13}$C NMR spectrum with signals at about and 113.1, 133.1, 160.9±0.2 ppm;
a solid-state $^{13}$C NMR spectrum having chemical shifts differences between the signal exhibiting the lowest chemical shift and another in the chemical shift range of 100 to 180 ppm of about 9.2, 29.2 and 57.0±0.1 ppm, wherein the signal exhibiting the lowest chemical shift in the chemical shift area of 100 to 180 ppm is typically at about 103.9±1 ppm;
a $^{13}$C NMR spectrum as depicted in FIG. 21;
a $^{13}$C NMR spectrum as depicted in FIG. 22; and
combinations thereof; wherein said crystalline form is anhydrous.

27. The crystalline Nilotinib HCl of claim 26, characterized by an x-ray powder diffraction pattern having peaks at about 5.7, 9.8, 15.0, 15.8 and 17.3 degrees two theta±0.2 degrees two theta.

28. The crystalline Nilotinib HCl of claim 27, further characterized by x-ray powder diffraction peaks at about 7.5, 11.4, 18.6, 19.6 and 20.7 degrees two theta±0.2 degrees two theta.

* * * * *